(12) United States Patent
Wight et al.

(10) Patent No.: US 8,410,067 B2
(45) Date of Patent: Apr. 2, 2013

(54) INHIBITION OF VERSICAN WITH SIRNA AND OTHER MOLECULES

(75) Inventors: Thomas N. Wight, Seattle, WA (US); Mervyn John Merrilees, Auckland (NZ)

(73) Assignee: Benaroya Research Institute, Seattle, WA (US)

( * ) Notice: Subject to any disclaimer, the term of this patent is extended or adjusted under 35 U.S.C. 154(b) by 162 days.

(21) Appl. No.: 12/677,435

(22) PCT Filed: Oct. 31, 2008

(86) PCT No.: PCT/US2008/012359
§ 371 (c)(1),
(2), (4) Date: Apr. 7, 2010

(87) PCT Pub. No.: WO2009/061368
PCT Pub. Date: May 14, 2009

(65) Prior Publication Data
US 2011/0008366 A1    Jan. 13, 2011

Related U.S. Application Data

(60) Provisional application No. 60/985,766, filed on Nov. 6, 2007, provisional application No. 61/026,005, filed on Feb. 4, 2008.

(51) Int. Cl.
*C12N 15/11* (2006.01)
*C12Q 1/68* (2006.01)
*C07H 21/04* (2006.01)
*C07H 21/02* (2006.01)

(52) U.S. Cl. .................... 514/44 A; 536/23.1; 536/24.5; 435/6.1

(58) Field of Classification Search .................. None
See application file for complete search history.

(56) References Cited

U.S. PATENT DOCUMENTS

| 7,816,335 B2 * | 10/2010 | Wight et al. | 514/44 R |
| 2004/0213762 A1 * | 10/2004 | Wight et al. | 424/93.2 |
| 2005/0118157 A1 | 6/2005 | McMahon et al. | |
| 2007/0219152 A1 | 9/2007 | Schreiber et al. | |
| 2011/0124567 A1 * | 5/2011 | Wight et al. | 514/16.4 |

OTHER PUBLICATIONS

Wight et al., Circulation Research, 2004; 94:1158-1167.*
Matsuura et al., J. Pathology, 1996; 180:311-316.*
Creighton CJ et al. Analysis of tumor-host interactions by gene expression profiling of lung adenocarcinoma xenografts identifies genes involved in tumor formation. Molecular Cancer Research. Mar. 2005; 3(3): 119-129.
Arslan F et al. The role of versican isoforms V0/V1 in glioma migration mediated by transforming growth factor-beta2. British Journal of Cancer. May 2007; 96(10): 1560-1568.
Altman LC et al. Versican is required for hyaluronan (HA) dependent poly I:C stimulated leukocyte binding to human lung fibroblasts (HLF). Journal of Allergy and Clinical Immunology. Feb. 2006. 117(2): p. S3.
Supplementary European Search Report and Opinion, EP 08 84 8476, mailed Sep. 14, 2011.
Bensadoun ES et al. Proteoglycan deposition in pulmonary fibrosis. Am. J. Respir. Crit. Care Med. Dec. 1996; 154(6): 1819-1828. Abstract.
Sheng W et al. The roles of versican vi and v2 isoforms in cell proliferation and apoptosis. Molecular Biology of the Cell. Mar. 2005; 16: 1330-1340.
International Search Report and Written Opinion, PCT/US2008/012359, mailed Apr. 9, 2009.

* cited by examiner

*Primary Examiner* — Doug Schultz
(74) *Attorney, Agent, or Firm* — Myers Bigel Sibley & Sajovec, P.A.

(57) ABSTRACT

The present invention provides methods of treating disease or condition in a subject in need thereof, comprising administering the subject a versican inhibitor in an amount effective to treat the disease or condition. Example diseases or conditions include, but are not limited to, fibrotic disease such as fibrotic lung disease, restenosis such as arterial restenosis, atherosclerosis, cancer, and inflammatory disease. Compounds and compositions for carrying out such a method are also described.

5 Claims, 23 Drawing Sheets

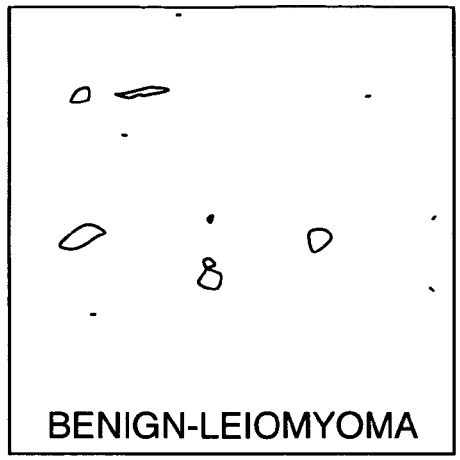
FIG. 1-1A BENIGN-LEIOMYOMA
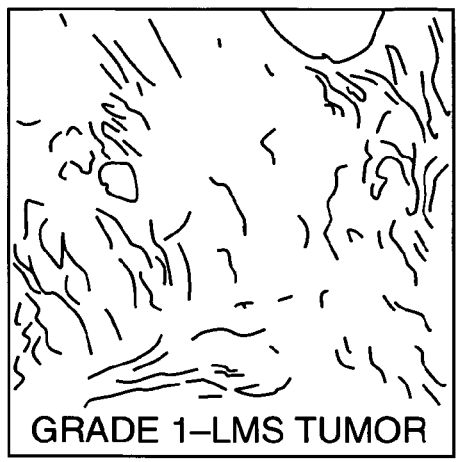
FIG. 1-1B GRADE 1–LMS TUMOR
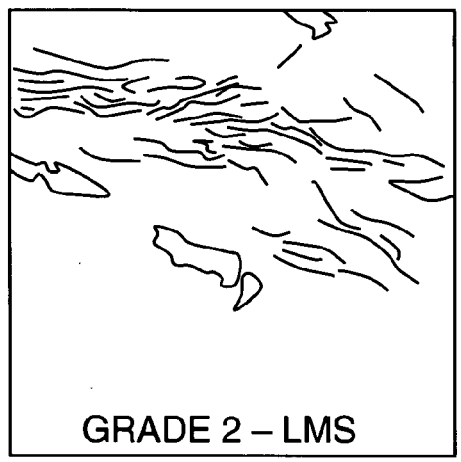
FIG. 1-1C GRADE 2 – LMS
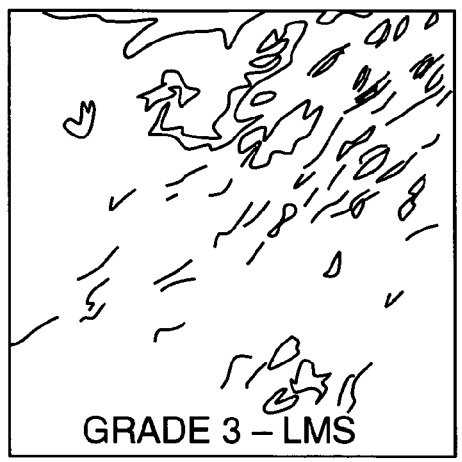
FIG. 1-1D GRADE 3 – LMS
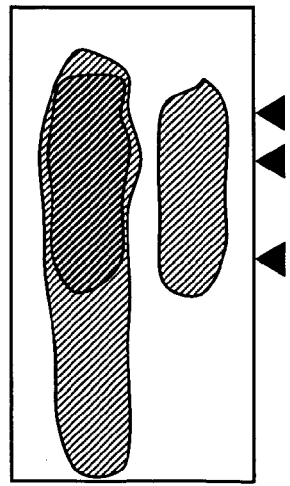
FIG. 1-1E LMS TUMOR    NORMAL MYOMETRIUM

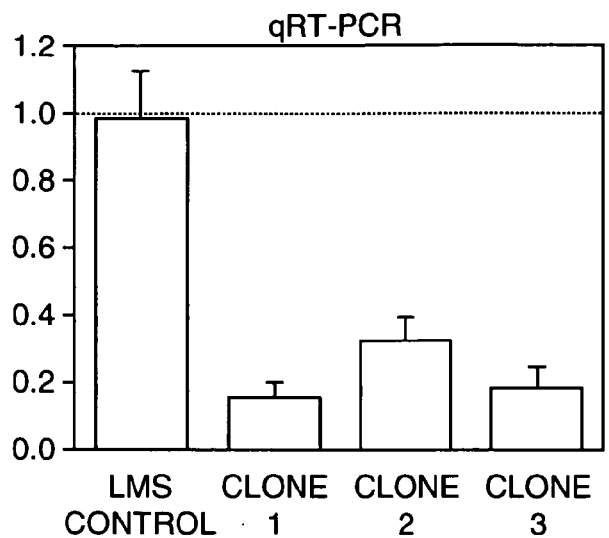
*FIG. 1-2A*
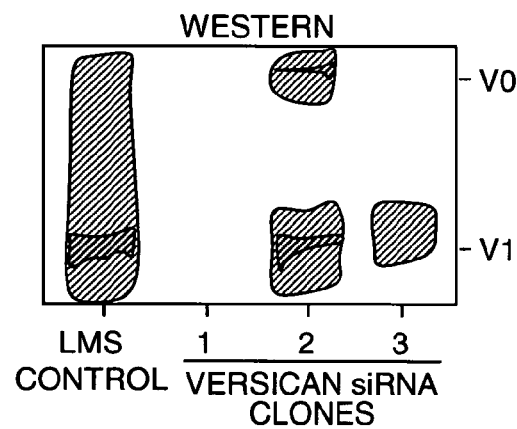
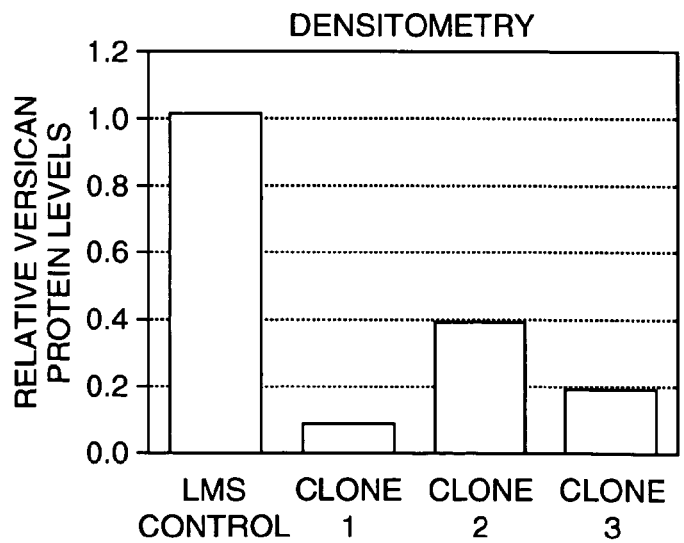
*FIG. 1-2B*

LMS3.1-1

VERSICAN siRNA

LMS3.1-1

VERSICAN siRNA

LM = LIGHT MICROSCOPY
EM = ELECTRON MICROSCOPY

LXSN
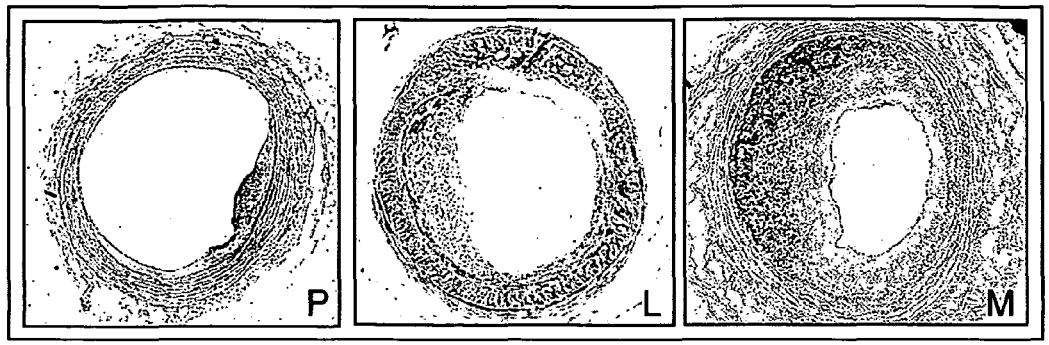
V3
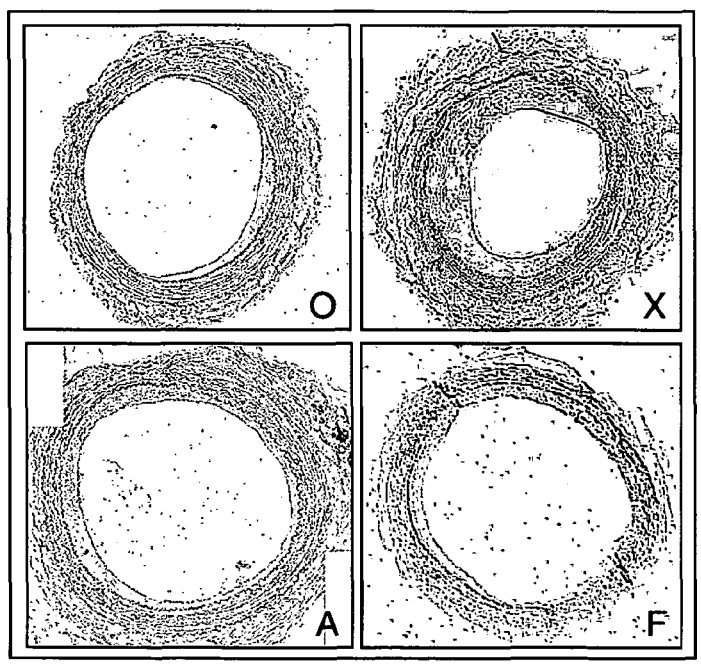
ANTISENSE
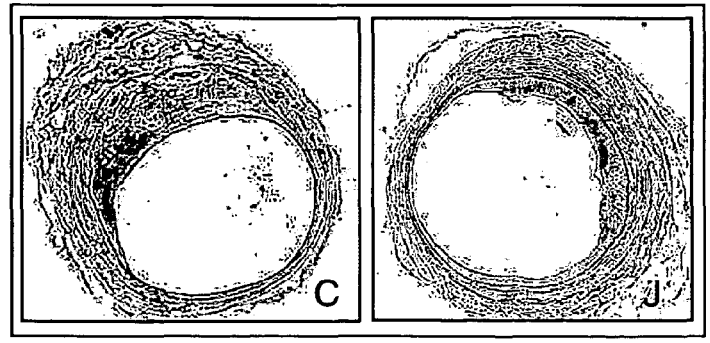
*FIG. 2-5*

P LXSN
L LXSN
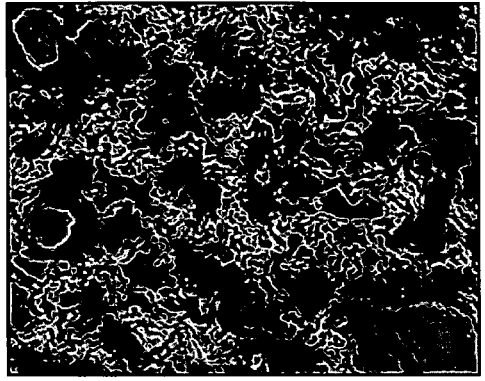
M LXSN
F V3
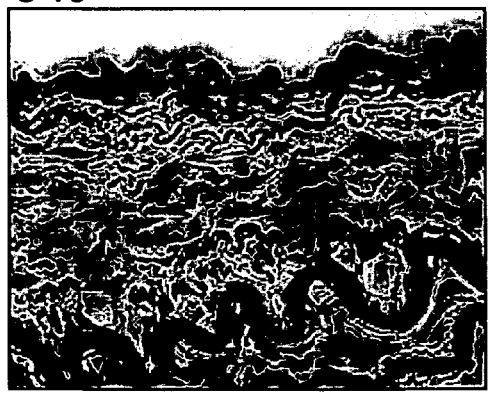
O V3
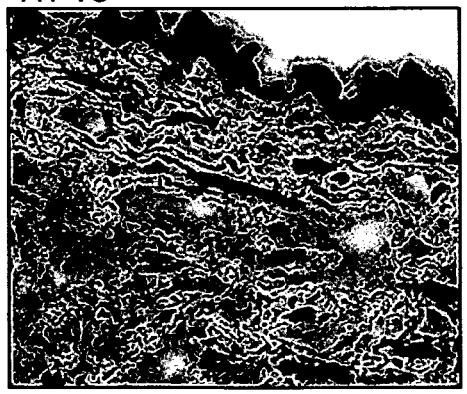
A1 V3
C1 ANTISENSE
J ANTISENSE
*FIG. 2-10*

P LXSN 
L LXSN 
M LXSN 
F V3 
O V3 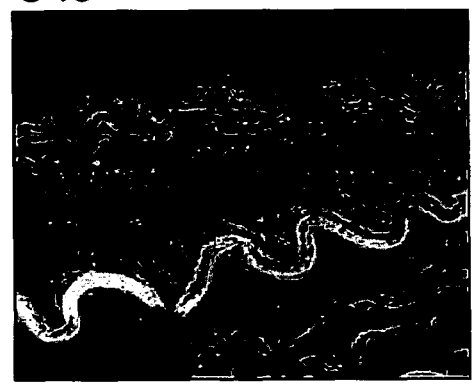
A1 V3 
C1 ANTISENSE 
J ANTISENSE 
FIG. 2-11

SEQUENCE LISTING

<160> NUMBER OF SEQ ID NOS: 1

<210> SEQ ID NO 1
<211> LENGTH: 64
<212> TYPE: DNA
<213> ORGANISM: Artificial
<220> FEATURE:
<223> OTHER INFORMATION: siRNA versican inhibitory sequence

<400> SEQUENCE: 1
gatcccaatt caccttcgag gaggcttcaa gagagcctcc tcgaaggtga attttttttg    60
gaaa                                                                 64

INHIBITION OF VERSICAN WITH SIRNA AND OTHER MOLECULES

RELATED APPLICATIONS

This application is a 35 U.S.C. §371 national phase application of PCT Application PCT/US2008/012359, filed Oct. 31, 2008, and published in English on May 14, 2009, as International Publication No. WO 2009/061368, and which claims the benefit under 35 U.S.C. §119(e) of U.S. Provisional Patent Application Ser. No. 60/985,766, filed Nov. 6, 2007, and U.S. Provisional Patent Application Ser. No. 61/026,005, filed Feb. 4, 2008, the disclosure of each of which is incorporated herein by reference in its entirety.

FIELD OF THE INVENTION

This invention relates to versican inhibitors, methods of using the same, and compositions thereof.

BACKGROUND OF THE INVENTION

Wight and Merrilees, *Therapeutic Compounds and Methods*, US Patent Application No. 2004/0213762 (Published Oct. 28, 2004), describes compounds and methods that modulate the activity of versican isoform V3.

T. Wight and M. Merrilees, *Circ. Res.* 94, 1158-1167 (2004) review the roles of proteoglycans such as versican in atherosclerosis and restenosis.

A. Hinek et al., *Am. J. Pathol.* 164, 119-141 (2004) describes the effect of retrovirally mediated overexpression of versican V3 on elastogenesis and heightened proliferation exhibited by fibroblasts from Costello Syndrome and Hurler disease patients.

SUMMARY OF THE INVENTION

A first aspect of the present invention is a method of treating a fibrotic disease in a subject in need thereof, comprising administering the subject a versican inhibitor in an amount effective to treat the fibrotic disease.

A further aspect of the present invention is a method of treating restenosis in a subject in need thereof, comprising administering the subject a versican inhibitor in an amount effective to inhibit arterial restenosis.

A further aspect of the present invention is a method of treating atherosclerosis in a subject in need thereof, comprising administering the subject a versican inhibitor in an amount effective to treat the atherosclerosis.

A further aspect of the present invention is a method of treating cancer in a subject in need thereof, comprising administering the subject a versican inhibitor in an amount effective to treat the cancer (e.g., by inhibiting tumor progression or inhibiting metastasis).

A further aspect of the present invention is a method of treating a fibrotic lung disease in a subject in need thereof, comprising administering the subject (e.g., by inhalation administration) a versican inhibitor in an amount effective to treat the fibrotic lung disease. Examples of fibrotic lung disease include, but are not limited to, cystic fibrosis, pulmonary fibrosis, and emphysema (including emphysematous changes).

A further aspect of the invention is a method of treating an inflammatory disease in a subject in need thereof, comprising administering the subject (e.g., by inhalation administration) a versican inhibitor in an amount effective to treat the inflammatory disease. Examples of inflammatory diseases include, but are not limited to, chronic bronchitis, asthma, and atherosclerosis.

A further aspect of the present invention is a method of inhibiting scar tissue formation in a subject in need thereof, comprising administering the subject a versican inhibitor in an amount effective to inhibit scar tissue formation. In some embodiments, the administering step is carried out by topically applying the versican inhibitor to an injured region at risk of developing a scar.

A further aspect of the present invention is, in a method of growing mammalian tissue in vitro, the improvement comprising administering to the tissue in vitro versican inhibitor in an amount effective to promote elastin fiber formation therein.

A further aspect of the present invention is a biomedical implant having a versican inhibitor covalently or noncovalently coupled thereto.

In some embodiments of the foregoing, the versican inhibitor is an siRNA molecule comprising a double-stranded segment 15-60 nucleotides in length, wherein the siRNA molecule inhibits expression of versican in a subject or tissue.

In some embodiments of the foregoing, the versican inhibitor is an antibody that specifically binds to versican.

A further aspect of the present invention is a composition comprising a versican inhibitor as described herein in a pharmaceutically acceptable carrier.

A further aspect of the present invention is the use of a versican inhibitor as described herein for the preparation of a medicament for carrying out a method as described herein.

The present invention is explained in greater detail in the drawings herein and the specification set forth below. The disclosures of all United States Patent references cited herein are to be incorporated by reference herein in their entirety.

BRIEF DESCRIPTION OF THE DRAWINGS

FIG. 1-1. Versican is highly expressed in leiomyosarcoma tissue. (A-D) Four grades of SMC tumor (benign leiomyoma, and LMS grades 1-3) were assessed histologically for their versican expression patterns. Grade 1 and Grade 2 LMS tumors (B,C) displayed the greatest versican expression in terms of both intensity and distribution. The increased cellularity in lower grade tumors appeared to correspond to areas of high versican expression. Original magnification 400×. (E) Northern blot analyses of LMS tissue show a high level of versican transcript versus normal, non-lesional tissue. Arrowheads (◄) indicate versican isoform bands. (F) Densitometry of versican isoform northern blot bands combined shows LMS tumor having significantly greater mRNA levels versus adjacent myometrial controls.

FIG. 1-2. (A) By constitutive expression of 1059 siRNA were ware able to achieve as much as 85% knockdown in versican mRNA and 95% versican protein (B). (C) Immunohistochemical analysis confirmed that versican levels were significantly reduced in the versican knockdown SMCs.

FIG. 1-3. $^3$H-Thymidine, proliferation and versican add-back data. $^3$H-Thymidine levels (A) and growth curve (B) indicate that the LMS 3.1 empty vector control cells divide and proliferate at a significantly higher rate than the Versican siRNA cells. (C) The reduction in the proliferative rate induced by versican siRNA can be reversed by the addition of purified versican to the culture medium. The exogenous versican exerts its effect in a dose-dependent manner.

FIG. 1-4. Differential trypsinization. (A) Using 0.05% trypsin, it took approximately 10× as much time for all the cells to be completely removed from the standard tissue culture plastic (n=6). (B) Upon trypsinization, siRNA cells were removed significantly faster with the addition of versican (p<0.0001).

FIG. 1-5. Morphological consequences of versican directed siRNA on cells in culture. Empty-vector control LMS cells growing from clonal islands assume spindle shapes typical of smooth muscle cells (A). In contrast, LMS cells expressing versican siRNA (B) are flatter and more polygonal. These differences in cell shape are associated with differences in migratory capacity. In scratch wound assays (C,D) the migration of control LMS cells was significantly greater at 12 and 24 hours than that of LMS cells expressing versican siRNA.

FIG. 1-6. Reduction in HA and HA synthase levels with the reduction of versican synthesis. (A) A decrease in HA production levels followed versican levels knocked down by siRNA. Versican siRNA clones along with normal uterine SMC controls produce significantly less total HA and on a per cell basis. (B) RT-PCR for HAS2, HAS3 and versican compared empty vector 3.1 LMS cells and LMS cells in which versican mRNA has been constitutively reduced using versican directed siRNA. (C) Densitometry of RT-PCR averaged control (n=4) or siRNA clones (n=3) showed a significant reduction in the levels of HAS2, HAS3, and versican in the cells expressing versican siRNA. All lanes were normalized to GAPDH.

FIG. 1-7. Large molecular weight HA by itself does not restore the proliferative profile of versican siRNA cells, but does with the addition of purified versican. Although there is a significant increase in cell proliferation with the addition of HA (30 µg/ml; p<0.015), the increase due to the addition of versican at ng levels is significantly greater, and near complete restoration (96.6%) of cell native proliferative rate is achieved at 100 µg/ml versican. The difference between versican alone and versican+large HA is significant (p<0.004) suggesting an additive or synergistic effect between HA and versican on cell proliferation.

FIG. 1-8. in vivo IHC analysis. Images represent subcutaneous tumors excised after 21 days in nude mouse; all image pairs were taken at equal exposure. The constitutively expressing LMS versican siRNA cells (right two panels) only faintly express versican (B) and HA (D) compared to the tumors of the empty vector control panels on the left (A-versican, C-HA).

FIG. 1-9. in vivo analysis. (A) Tumor volume over time in nude mice injected subcutaneously; LMS 3.1 empty vector control cells (—▲—) versus versican siRNA LMS cells (—□—). (B) Mitotic index of Vc siRNA versus LMS control cells. Values are expressed as mitotic figures per 10-400× fields; both the range of values and average are depicted.

FIG. 2-1 Diagram showing methodology of transduction, culture and seeding of retrovirally-transduced vascular rabbit smooth muscle cells. Approximately 50,000 cells in a volume of 0.1 ml of serum-free media were seeded into each balloon-damaged carotid using a flexible catheter and left to settle and attach for 15 minutes before heparin flushing and re-establishment of normal blood flow.

FIG. 2-2 Summary of the experimental protocol following cell seeding. Three groups of animals were established; animals seeded with LXSN control (vector only) cells, V3 transduced cells, and antisense transduced cells. All groups were maintained on normal chow for four weeks before being placed on a cholesterol diet for a further 4 weeks (with a stepped increase at week 6). Weight and plasma cholesterol measurements were determined as shown.

FIG. 2-3 Plasma cholesterol by treatment-group showing that levels were similar for all groups at each time point.

FIG. 2-4 Diagram and photograph of a perfusion-fixed (100 mmHg, 4% paraformaldehyde) vessel showing regions sampled during analysis.

FIG. 2-5 Low power transverse sections of carotids of representative animals from each group stained with Oil red O to show lipid deposition. Intimal thickness and lipid staining were reduced in the V3 and antisense animals (see FIG. 2-6 for morphometric analyses).

FIG. 2-6 Histograms of intimal depth and amount of lipid in LXSN control, antisense and V3 vessels. Intimal depth is the mean depth (±SE). For each animal a total of 80 measurements were taken from 10 sections (5 sections from LM1 and 5 sections from LM2—see FIG. 4) spaced at 1 mm intervals. Four random measurements were made on each section according to clock face positions of 3, 6 and 9 and 12. The mean value for each animal was used to calculate an overall mean for the group. The amount of lipid (±SE) was determined using NIH Image to calculate staining intensity and expressed as total lipid and as % lipid relative to intimal area. Mean values for each animal were used to calculate an overall mean. Significance values were determined by Student's T Test.

FIG. 2-7 LXSN control vessel showing thickened intima rich containing lipid deposits (stained with Oil red O) and scattered deposits of elastin (stained with orcein). Elastin deposits are also visible by fluorescence microscopy due to their autofluorescence.

FIG. 2-8 LXSN control vessel with less extensive lipid deposits. Not that neither the lipid stained areas or nor the non-lipid areas contain elastic fibers, rather scattered deposits of elastin only.

FIG. 2-9 V3 vessel showing the absence of lipid staining in a thin intima and the presence of numerous elastic fibers, visible by both orcein staining and autofluorescence, arranged circumferentially.

FIG. 2-10 Summary figure comparing orcein-stained elastin in intimae of three LXSN vessels, three V3 vessels, and two antisense vessels. Prominent elastic fibers are present in the intimae of the V3 and antisense vessels, in contrast to the vector-only control vessels which contain scattered deposits of elastin.

FIG. 2-11 Summary figure of autofluorescence of the vessels shown in FIG. 10, demonstrating prominent arrays of elastic fibers in the neointimae of the V3 and antisense vessels.

FIG. 3. Inhibition of monocyte retention by interference with ECM formation in poly I:C-treated cells.

FIG. 4. Reduced macrophage (RAM11) and lipid (Oil red O) staining in ballooned-injured rabbit carotid arteries seeded with V3 overexpressing SMC compared with vector-alone (LXSN) cells. Animals were fed a normal chow diet for 4 weeks followed by 4 weeks on a cholesterol (0.3%) diet. Plasma cholesterol averaged 25 mmol/l.

DETAILED DESCRIPTION OF THE PREFERRED EMBODIMENTS

I. Definitions

Figures 1, 2, 2C:
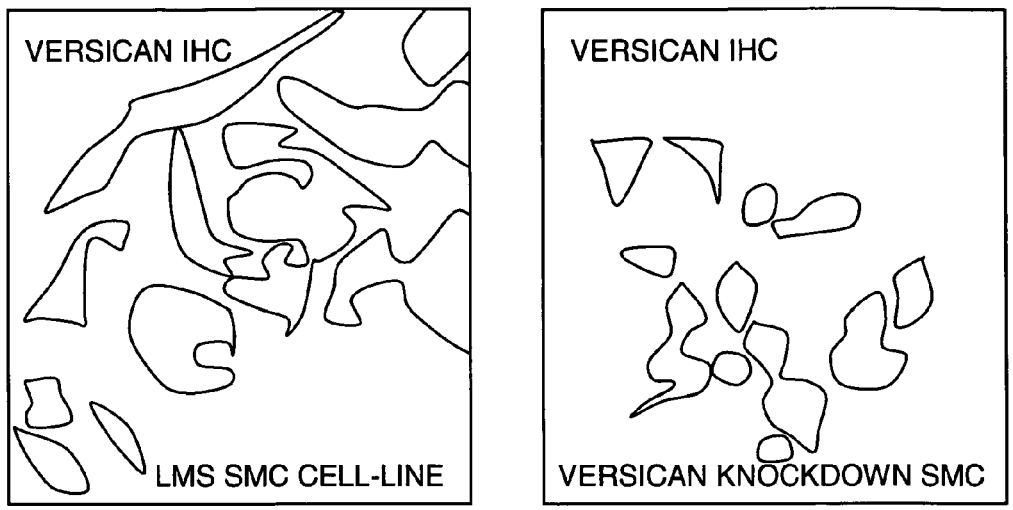

"Subjects" as used herein are generally human subjects, but may also be other animal (typically mammalian) subjects such as dogs, cats, horses, cows, sheep, monkey, chimpanzee, etc., for veterinary purposes.

"Fibrotic disease" as used herein may be any fibrotic disease, including but not limited to undesired scar tissue formation (e.g., in response to surgical incision or traumatic injury, such as for improved cosmetic outcome), schistosoma japonicum infection, rheumatoid arthritis, lupus, pathogenic fibrosis, fibrosing disease, fibrotic lesion, radiation damage, autoimmune disease, Lyme disease, chemotherapy induced fibrosis, HIV, infection-induced focal sclerosis, failed back syndrome, abdominal adhesion post surgery scarring, fibrocystic formation, fibrosis after spinal injury, surgery-induced fibrosis, mucosal fibrosis, peritoneal fibrosis caused by dialysis, and Adalimumab-associated pulmonary fibrosis, as well as fibrotic diseases of various organs and tissues such as the liver, kidney, lung, heart, eye, skin, mouth or esophagus, pancreas, gastrointestinal tract, etc. See, e.g., R. Gomer and D. Pilling, US Patent Application Publication No. 2007/0065866 (Mar. 22, 2007). Examples of fibrosing disease of the liver include but are not limited to: alcohol, drug, and/or chemically induced cirrhosis, ischemia-reperfusion injury after hepatic transplant, necrotizing hepatitis, hepatitis B, hepatitis C, primary biliary cirrhosis, and primary sclerosing cholangitis. Examples of fibrosing diseases of the kidney include but are not limited to proliferative glomerulonephritis, sclerosing glomerulonephritis, nephrogenic fibrosing dermopathy, diabetic nephropathy, renal tubulointerstitial fibrosis, and focal segmental glomerulosclerosis. Examples of fibrosing diseases of the lung include but are not limited to: pulmonary interstitial fibrosis, sarcoidosis, pulmonary fibrosis, idiopathic pulmonary fibrosis, asthfila; chronic obstructive pulmonary disease, diffuse alveolar damage disease, pulmonary hypertension, neonatal bronchopulmonary dysplasia, chronic asthma, and emphysema (including emphysematous changes). Examples of fibrosing disease of the heart include but are not limited to: myocardial fibrosis, atherosclerosis, coronary artery restenosis, congestive cardiomyopathy, and heart failure. Examples of fibrosing diseases of the eye include but are not limited to: exophthalmos of Grave's disease, proliferative vitreoretinopathy, anterior capsule cataract, corneal fibrosis, corneal scarring due to surgery, trabeculectomy-induced fibrosis, progressive subretinal fibrosis, and multifocal granulomatous chorioretinitis. Examples of fibrosing diseases of the skin include but are not limited to: Depuytren's contracture, scleroderma, keloid scarring, psoriasis, hypertrophic scarring, atherosclerosis, restenosis, and psuedoscleroderma. Examples of fibrosing diseases of the mouth and/or esophagus include but are not limited to: periodontal disease scarring, gingival hypertrophy secondary to drugs, and congenital esophageal stenosis. Examples of fibrosing diseases of the pancreas include but are not limited to: pancreatic fibrosis, stromal remodeling pancreatitis, and stromal fibrosis. Examples of fibrosing diseases of the gastrointestinal tract include but are not limited to: collagenous colitis, villous atrophy, crypt hyperplasia, polyp formation, fibrosis of Crohn's disease, and healing gastric ulcer. An example of a fibrosing disease of the brain is glial scar tissue formation. Examples of fibrosing diseases of the breast include but are not limited to: fibrocystic disease and desmoplastic reaction to breast cancer. Fibrosing diseases of the bone marrow include but are not limited to: myelodysplasia and neoplastic diseases. Fibrosing diseases of the bone include rheumatoid pannus formation. Examples of fibrosing disease of the genitourinary system include but are not limited to: endometriosis, uterine fibroids, ovarian fibroids, Peyronie's disease. Examples of other fibrosing disease include fibrosing disease relating to radiation treatment of head and neck cancer, ovarian cancer, prostate cancer, lung cancer, gastrointestinal cancer, colon cancer and breast cancer. See, e.g., US Pat. Application No. 2007/0065866 to Gomer et al.

"Restenosis" as used herein refers to the re-narrowing of an artery after an initially successful angioplasty due to exaggerated healing which causes a proliferation of tissue in the angioplasty area, and includes both re-narrowing restenosis and chronic reclosure restenosis. Re-narrowing or acute restenosis of an artery after angioplasty occurs in 10 to 50% of patients undergoing this procedure and subsequently requires either further angioplasty or more invasive surgical procedures. Chronic reclosure restenosis after angioplasty is a more gradual process than acute reocclusion: 30% of patients with subtotal lesions and 50% of patients with chronic total lesions will go on to restenosis after angioplasty. See, e.g., H. Sahota, U.S. Pat. No. 7,241,284.

"Cancer" as used herein includes but is not limited to breast, colon, lung, prostate, liver, ovarian, skin (e.g., melanoma, carcinoma), and pancreatic cancer, etc. Cancer as used herein includes mesenchymal cancers (sarcomas) such as leiomyosarcoma.

"Arteriosclerosis" as used herein refers to any condition in which the arteries become hard and less flexible.

"Atherosclerosis" as used herein refers to the build-up of a waxy deposit in the intima and inner media of blood vessels. Atherosclerosis is a form of arteriosclerosis.

"Versican" is a member of the large chondroitin sulfate proteoglycan (CSPG) family. The versican core protein and nucleic acid sequence encoding the same is known. See, e.g., E. Ruoslahti, U.S. Pat. No. 5,180,808; Wight and Merrilees, US Patent Application 2004/0213762. Versican as described herein is typically mammalian, including but not limited to human, cat, dog, monkey, mouse, rat, etc. Versican as described herein may be of any isoform, including V0, V1, and V3.

"Versican inhibitor" as used herein may be any versican inhibitor, including but not limited to peptides, proteins (e.g., the V3 molecule or a truncated versican thereof without the polysaccharide, with a modified or truncated polysaccharide), nucleic acids such as antisense nucleic acids, antibodies, siRNAs, small organic compounds, etc., as for example described further below or in Wight and Merrilees, *Therapeutic Compounds and Methods*, US Patent Application No. 2004/0213762 (Published Oct. 28, 2004). Thus the inhibitor can be a competitive inhibitor (e.g., exogenous V3 competing with bound versican for substrate, a direct inhibitor (e.g., antibody blocking the extracellular portion of versican to prevent binding, a down-regulator of versican expression (e.g., an siRNA), etc. In some embodiments, the versican inhibitor competitively inhibits the binding of versican to one or two or more of CD44, the EGF receptor, Tenascin R, PSGL-1, hyaluronan, fibronectin, and/or Apolipoprotein B-containing lipoproteins.

"Antibody" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, and may be chimeric or "humanized" antibodies. See, e.g., M. Walker et al., *Molec. Immunol.* 26, 403-11 (1989). The antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in SegAl et al., U.S. Pat. No. 4,676,980.

"Interfering RNA" or "RNAi" or "interfering RNA sequence" refers to double-stranded RNA (i.e., duplex RNA) that is capable of silencing, reducing, or inhibiting expression of a target gene (i.e., by mediating the degradation of mRNAs which are complementary to the sequence of the interfering RNA) when the interfering RNA is in the same cell as the target gene. Interfering RNA thus refers to the double-stranded RNA formed by two complementary strands or by a single, self-complementary strand. Interfering RNA may have substantial or complete identity to the target gene or may comprise a region of mismatch (i.e., a mismatch motif). The sequence of the interfering RNA can correspond to the full length target gene, or a subsequence thereof. Interfering RNA includes "small-interfering RNA" or "siRNA," See, e.g., I. MacLachlan et al., US Patent Application No. 2007/0218122 (Published Sep. 20, 2007).

"Small-interfering RNA" or "siRNA," are typically e.g., interfering RNA of about 15-60, 15-50, or 15-40 (duplex) nucleotides in length, more typically about 15-30, 15-25, or 19-25 (duplex) nucleotides in length (e.g., each complementary sequence of the double-stranded siRNA is 15-60, 15-50, 15-40, 15-30, 15-25, or 19-25 nucleotides in length, and the double-stranded siRNA is about 15-60, 15-50, 15-40, 15-30, 15-25, or 19-25 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single-stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. The siRNA can be chemically synthesized or may be encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., Proc. Natl. Acad. Sci. USA, 99:9942-9947 (2002); Calegari et al., Proc. Natl. Acad. Sci. USA, 99:14236-14240 (2002); Byrom et al., Ambion TechNotes, 10:4-6 (2003); Kawasaki et al., Nucleic Acids Res., 31:981-987 (2003); Knight et al., Science, 293:2269-2271 (2001); and Robertson et al., J. Biol. Chem., 243:82-91 (1968)). Preferably, dsRNA are at least 50 nucleotides to about 100, 200, 300, 400, or 500 nucleotides in length. A dsRNA may be as long as 1000, 1500, 2000, or 5000 nucleotides in length, or longer. The dsRNA can encode for an entire gene transcript or a partial gene transcript.

"Biomedical implant" as used herein may be formed of any suitable material, including but not limited to metals, semiconductors, synthetic polymers, natural organic polymers (which polymers may be biodegradable or inert), composites thereof, etc. Examples include but are not limited to stents, fasteners, ports, catheters and guides, tissue scaffolds, and tissue grafts such as aortic grafts.

II. Antibody Versican Inhibitor Active Agents

Antibodies, including both monoclonal and polyclonal antibodies, that bind to versican are known (see, e.g., E. Ruoslahti, U.S. Pat. No. 5,180,808; see also S. Cattaruzza et al., *J. Biol. Chem.* 277, 47626 (2002)). One example of suitable antibodies is given in Example 3 below. Additional antibodies that bind or specifically bind to versican can be produced in accordance with known techniques or variations thereof that will be apparent to those skilled in the art.

III. siRNA Versican Inhibitor Active Agents siRNAs as active agents for inhibiting expression of target genes in general are known. See, e.g., U.S. Pat. No. 6,506,559 to Fire and Mellow; see also U.S. Pat. No. 7,056,704 to Tuschi et al., U.S. Pat. No. 7,078,196 to Tuschi et al., U.S. Pat. No. 6,107,094 to Crooke, U.S. Pat. No. 5,898,221 to Crook, and U.S. Pat. No. 6,573,099 to Benitec. Recent overviews of siRNAs and formulations thereof include but are not limited to that set forth in MacLachlan et al., US Patent Application No. 2007/0218122

The present invention provides an interfering RNA that inhibits or silences (e.g., partially or completely inhibits) expression of a versican gene. An interfering RNA can be provided in several forms. For example, an interfering RNA can be provided as one or more isolated small-interfering RNA (siRNA) duplexes, longer double-stranded RNA (dsRNA), or as siRNA or dsRNA transcribed from a transcriptional cassette in a DNA plasmid. The interfering RNA may also be chemically synthesized. The interfering RNA can be administered alone or co-administered (i.e., concurrently or consecutively) with conventional agents used to treat the condition with which the subject is afflicted In certain embodiments, the siRNA molecules of the present invention are chemically modified In some embodiments, the modified siRNA contains at least one 2'-O-methyl (2'OMe) purine or pyrimidine nucleotide such as a 2'OMe-guanosine, 2'OMe-uridine, 2'OMe-adenosine, and/or 2'OMe-cytosine nucleotide.

In some embodiments, the siRNA molecules described herein comprise at least one region of mismatch with its target sequence. As used herein, the term "region of mismatch" refers to a region of an siRNA that does not have 100% complementarity to its target sequence. An siRNA may have at least one, two, or three regions of mismatch. The regions of mismatch may be contiguous or may be separated by one or more nucleotides. The regions of mismatch may comprise a single nucleotide or may comprise two, three, four, or more nucleotides.

A. Selection of siRNA Sequences. Suitable siRNA sequences can be identified using any means known in the art. Typically, the methods described in Elbashir et al., Nature, 411:494-498 (2001) and Elbashir et al., EMBO J., 20:6877-6888 (2001) are combined with rational design rules set forth in Reynolds et al., Nature Biotech., 22:326-330 (2004).

Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., EMBO J., 20:6877-6888 (2001)). The nucleotides immediately 3' to the dinucleotide sequences are identified as potential siRNA target sequences. Typically, the 19, 21, 23, 25, 27, 29, 31, 33, 35, or more nucleotides immediately 3' to the dinucleotide sequences are identified as potential siRNA target sites. In some embodiments, the dinucleotide sequence is an AA or NA sequence and the 19 nucleotides immediately 3' to the AA or NA dinucleotide are identified as a potential siRNA target site. siRNA target sites are usually spaced at different positions along the length of the target gene. To further enhance silencing efficiency of the siRNA sequences, potential siRNA target sites may be analyzed to identify sites that do not contain regions of homology to other coding sequences, e.g., in the target cell or organism. For example, a suitable siRNA target site of about 21 base pairs typically will not have more than 16-17 contiguous base pairs of homology to coding sequences in the target cell or organism. If the siRNA sequences are to be expressed from an RNA Pol III promoter, siRNA target sequences lacking more than 4 contiguous A's or T's are selected.

Once a potential siRNA sequence has been identified, the sequence can be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA are known. One of skill in the art will appreciate that sequences with one or more of the foregoing characteristics may be selected for further analysis and testing as potential siRNA sequences.

Additionally, potential siRNA target sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA target sequences may be further analyzed based on siRNA duplex asymmetry as described in, e.g., Khvorova et al., Cell, 115:209-216 (2003); and Schwarz et al., Cell, 115:199-208 (2003). In other embodiments, potential siRNA target sequences may be further analyzed based on secondary structure at the mRNA target site as described in, e.g., Luo et al., Biophys. Res. Commun., 318:303-310 (2004). For example, mRNA secondary structure can be modeled using the Mfold algorithm (available at http://www.bioinfo.rpi.edu/applications/mfold/ma/form1.cgi) to select siRNA sequences which favor accessibility at the mRNA target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3', 5'-UGU-3', 5'-GUGU-3', 5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naive mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-.alpha., IFN-.beta., IFN-.gamma., IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as to confirm that its immunostimulatory properties have been reduced or abrogated.

B. Generating siRNA Molecules. siRNA molecules can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al., Genes Dev., 15:188 (2001) or Nykanen et al., Cell, 107:309 (2001)), or may lack overhangs (i.e., have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Alternatively, one or more DNA plasmids encoding one or more siRNA templates are used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp et al., Science, 296:550 (2002); Donze et al., Nucleic Acids Res., 30:e46 (2002); Paddison et al., Genes Dev., 16:948 (2002); Yu et al., Proc. Natl. Acad. Sci. USA, 99:6047 (2002); Lee et al., Nat. Biotech., 20:500 (2002); Miyagishi et al., Nat. Biotech., 20:497 (2002); Paul et al., Nat. Biotech., 20:505 (2002); and Sui et al., Proc. Natl. Acad. Sci. USA, 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp et al., supra). The selected promoter can provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a target cell. It will be apparent to those of skill in the art that plasmids originally designed to express desired gene sequences can be modified to contain a transcriptional unit cassette for transcription of siRNA.

In some embodiments, siRNA molecules are chemically synthesized. The single-stranded molecules that comprise the siRNA molecule can be synthesized using any of a variety of techniques known in the art, such as those described in Usman et al., J. Am. Chem. Soc., 109:7845 (1987); Scaringe et al., Nucl. Acids Res., 18:5433 (1990); Wincott et al., Nucl. Acids Res., 23:2677-2684 (1995); and Wincott et al., Methods Mol. Bio., 74:59 (1997). The synthesis of the single-stranded molecules makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 .mu.mol scale protocol with a 2.5 min coupling step for 2'-O-methylated nucleotides. Alternatively, syntheses at the 0.2 .mu.mol scale can be performed on a 96-well plate synthesizer from Protogene (Palo Alto, Calif.). However, a larger or smaller scale of synthesis is also within the scope of the present invention. Suitable reagents for synthesis of the siRNA single-stranded molecules, methods for RNA deprotection, and methods for RNA purification are known to those of skill in the art.

The siRNA molecules can also be synthesized via a tandem synthesis technique, wherein both strands are synthesized as a single continuous fragment or strand separated by a cleavable linker that is subsequently cleaved to provide separate fragments or strands that hybridize to form the siRNA duplex. The linker can be a polynucleotide linker or a non-nucleoside linker. The tandem synthesis of siRNA can be readily adapted to both multiwell/multiplate synthesis platforms as well as large scale synthesis platforms employing batch reactors, synthesis columns, and the like. Alternatively, the siRNA molecules can be assembled from two distinct single-stranded molecules, wherein one strand comprises the sense strand and the other comprises the antisense strand of the siRNA. For example, each strand can be synthesized separately and joined together by hybridization or ligation following synthesis and/or deprotection. In certain other instances, the siRNA molecules can be synthesized as a single continuous fragment, where the self-complementary sense and antisense regions hybridize to form an siRNA duplex having hairpin secondary structure.

C. Modifying siRNA Sequences. In certain aspects, the siRNA molecules of the present invention comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, Principles of Nucleic Acid Structure, Springer-Verlag Ed. (1984), are also suitable for use in the siRNA molecules of the present invention. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. In certain instances, the siRNA molecules of the present invention include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., J. Am. Chem. Soc., 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, Nucl. Acids Res., 29:2437-2447 (2001)) can be incorporated into the siRNA molecules of the present invention.

In certain embodiments, the siRNA molecules of the present invention further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(.beta.-D-erythrofuranosyl) nucleotides, 4'-thio nucleotides, carbocyclic nucleotides, 1,5-anhydrohexitol nucleotides, L-nucleotides, .alpha.-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., Tetrahedron 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., Nucleic Acid Analogues: Synthesis and Properties, in Modern Synthetic Methods, VCH, 331-417 (1995); Mesmaeker et al., Novel Backbone Replacements for Oligonucleotides, in Carbohydrate Modifications in Antisense Research, ACS, 24-39 (1994)). Such chemical modifications can occur at the 5'-end and/or 3'-end of the sense strand, antisense strand, or both strands of the siRNA.

In some embodiments, the sense and/or antisense strand can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into the modified siRNA molecules of the present invention are described, e.g., in UK Patent No. GB 2,397,818 B and U.S. Patent Publication Nos. 20040192626 and 20050282188.

The siRNA molecules of the present invention can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5'- and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to the siRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and RNAi activity using any of a variety of well-known in vitro cell culture or in vivo animal models.

IV. Compositions and Administration

Active agents (siRNAs and antibodies) as described herein can be prepared as pharmaceutically acceptable compositions and administered in accordance with known techniques, or variations thereof that will be apparent to those skilled in the art. See, e.g., US Patent Application Publication No. 2007/0218122.

In one aspect, the present invention provides carrier systems containing the active siRNA molecules described herein. In some embodiments, the carrier system is a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a stabilized nucleic acid-lipid particle such as a SNALP or SPLP. One skilled in the art will appreciate that the siRNA molecules of the present invention can also be delivered as naked siRNA.

The active agents (siRNAs or antibodies) of the present invention can be administered either alone or in a mixture with a pharmaceutically-acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically-acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human.

The concentration of active agent in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

Systemic delivery for in vivo therapy, i.e., delivery of a therapeutic nucleic acid to a distal target cell via body systems such as the circulation, has been achieved using nucleic acid-lipid particles such as those disclosed in PCT Publication No. WO 96/40964 and U.S. Pat. Nos. 5,705,385; 5,976,567; 5,981,501; and 6,410,328. This latter format provides a fully encapsulated nucleic acid-lipid particle that protects the nucleic acid from nuclease degradation in serum, is nonimmunogenic, is small in size, and is suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has, also been discussed in Straubringer et al., Methods Enzymol., 101:512 (1983); Mannino et al., Biotechniques, 6:682 (1988); Nicolau et al., Crit. Rev. Ther. Drug Carrier Syst., 6:239 (1989); and Behr, Acc. Chem. Res., 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid-nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71(1994)).

The compositions of the present invention, either alone or in combination with other suitable components, can be made into aerosol formulations (i.e., they can be "nebulized") to be administered via inhalation (e.g., intranasally or intratracheally) (see, Brigham et al., Am. J. Sci., 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045.

Formulations suitable for parenteral administration, such as, for example, by intraarticular (in the joints), intravenous, intramuscular, intradermal, intraperitoneal, through catheters or ports, by subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the nucleic acid-lipid formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the nucleic acid-lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the nucleic acid-lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of the packaged nucleic acid (e.g., siRNA) suspended in diluents such as water, saline, or PEG 400; (b) capsules, sachets, or tablets, each containing a predetermined amount of the nucleic acid (e.g., siRNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the nucleic acid (e.g., siRNA) in a flavor, e.g., sucrose, as well as pastilles comprising the nucleic acid (e.g., siRNA) in an inert base, such as gelatin and glycerin or sucrose and acacia emulsions, gels, and the like containing, in addition to the nucleic acid (e.g., siRNA), carriers known in the art.

In another example of their use, nucleic acid-lipid particles can be incorporated into a broad range of topical dosage forms. For instance, the suspension containing the nucleic acid-lipid particles can be formulated and administered as gels, oils, emulsions, topical creams, pastes, ointments, lotions, foams, mousses, and the like.

The amount of active agent administered will depend upon the ratio of nucleic acid to lipid, the particular nucleic acid used, the disease state being diagnosed, the age, weight, and condition of the patient, and the judgment of the clinician, but will generally be between about 0.01 or 0.1 up to about 10, 30 or 50 mg per kilogram of body weight.

Combination treatments. The active compounds described herein can be administered alone or in combination with other compounds useful for the treatment of fibrotic diseases, such other compounds including but not limited to: anti-Fc-gamma-R antibodies, serum amyloid P (SAP), IL-12, laminin-1, IgG aggregates, cross-linked IgG (see, e.g., R. Gomer and D. Pilling, US Patent Application Publication No. 2007/0065866 (Mar. 22, 2007); R. Gomer and D. Pilling, US Patent Application Publication No. 2007/0065368 (Mar. 22, 2007), the compounds described in U.S. Pat. Nos. 7,166,625 and 7,026,342, or combinations thereof. Where administered in combination, the various compounds can be administered simultaneously or sequentially. Where administered simultaneously, the various compounds/active agents can be administered separately or together in the same pharmaceutically acceptable carrier.

V. In Vitro Tissue Culture Methods

As noted above, the present invention provides a method of growing mammalian tissue in vitro, the improvement comprising administering to the tissue in vitro versican inhibitor in an amount effective to promote elastin fiber formation therein. Culture techniques for the growth of mammalian tissue in vitro are known. See, e.g., U.S. Pat. Nos. 7,074,552; 6,544,762; 5,308,764. Tissues that may be grown include, but are not limited to, epithelial tissue, muscle tissue, connective tissue, and combinations thereof. A particular example is vascular tissue and or skin. Such tissues are useful for, among other things, the preparation of biomedical implants as described herein.

The present invention is explained in greater detail in the following non-limiting examples.

Example 1 siRNA Versican Inhibitors

Experimental

Leiomyosarcoma (LMS) is a mesenchymal form of cancer (sarcoma) that originates in dermis or deep soft tissues. LMS typically occurs in parenchymal organs, most often the uterus, but is also observed within large blood vessels such as the interior vena cava. Beyond surgical excision, there is presently no cure, and the disease is often fatal if not detected early. Although LMS can easily be recognized by its characteristic histological and immunophenotypical features, the etiology of the disease is unknown and remains uncharacterized.

The role of the extracellular matrix (ECM) in tumor biology has always been appreciated, but poorly understood. Specifically, are these molecules playing a role in the pathology or merely biproducts of the disease? Versican and hyaluronan (HA) are partnered ECM molecules that have been shown to play a major role in developmental biology (Faggian et al., 2007; Miosge et al., 1998), reproductive biology (Dunning et al., 2007; Irving-Rodgers et al., 2006), atherosclerotic vascular disease (Wight, 2002; Wight et al., 1997), and certain types of wound healing (Evanko et al., 1999; Geary et al., 1998). At the same time, expression levels of versican and HA (both separately and together) have been implicated as prognosis and or tumor grade markers in protate (Ricciardelli et al., 2007), breast (Suwiwat et al., 2004), lung (Pirinen et al., 2005), and ovarian cancers (Ricciardelli and Rogers, 2006). These molecules appear to play a central role in not only the growth of the tumor, but the metastatic potential.

Versican is a member of the large chondroitin sulfate proteoglycan (CSPG) family known to occur in four splice variants; V0, V1, V2 and V3. Common to these splice variants are the N- and C-terminal ends, or G-1 and G-3 domains respectively. The G-1 domain of versican contains an HA-binding region and is implicated as being responsible for the cell proliferation, adhesion, and migration charateristics mediated by versican (Yang et al., 1999), while the G-3 domain may well equally be involved in the cell phenotype control through its association with integrins (Wu et al., 2006), microfibrilar fibulins (Miosge et al., 1998), and EGF-Receptors (Xiang et al., 2006).

Versican's binding partner HA, is a large anionic polysaccharide shown to play roles in cell migration, adhesion and proliferation. HA is a an acidic glycosaminoglycan made entirely of a repeating disaccharide (D-glucuronic acid-β-1, 3-N-acetylglucosamine-β-1,4) units and is synthesized by one of three different yet related hyaluronan synthases, HAS1, HAS2 and HAS3. High levels of HA has also been used prognostically in cancer biology in terms of metastatic potential and tumor progression (Turley et al., 2002).

In initial studies, we found that the versican was highly expressed in LMS lesional tissue versus non-LMS tissue. Outside of development, the expression of versican at high levels in normal tissues is unusual. The high expression level of versican has been related to a number of cardiovascular and cancer pathologies, but not LMS.

We hypothesized that the misregulation or inappropriate expression of versican and or HA was part of LMS pathology. Within the last ten years the ability to specifically target genes without inducing off-target effects or induction of immune clearance has become possible with small interfering RNA (siRNA). The difference from previous targeting methodologies such as antisense or ribozyme gene-expression targeting is the size of the interfering molecule. siRNA was first reported by Fire et al., (1998) and is typically mediated by 19-22mer dsRNA, sense and antisense strands that anneal to form siRNA duplexes. In the design of siRNA, sequences unique only to the gene of interest can be identified against backdrop of the entire genome. One strand of the siRNA with 100% homology to the target sequence interacts with the mRNA for the target gene forming a RNA-induced silencing complex or RISC. The formation of the RISC complex brings to bare nucleases that cleave the target mRNA and is what ultimately leads to the specific silencing or knockdown of the target gene.

We, therefore, used a human uterine LMS tumor cell line, SK-LMS-1 (Fogh and Trempe, 1975), and a well established tumor cell growth model in nude mice (Horiuchi et al., 2000) to test the role of versican in the control of LMS cell phenotype. Using siRNA to specifically and selectively to target versican, we modified the LMS cells and determined the phenotypic changes that resulted. We observed that the knock-down of versican expression in LMS cells was accompanied by slower rates of proliferation and migration, and increased cell adhesion to the culture dish. We subsequently performed a pilot study using versican siRNA modulated LMS cells and unmodulated human LMS control cells to determine if the same reversal of phenotype was observed in vivo.

Methods

Analysis of versican expression in human LMS tumor samples. All tumor specimens were frozen and maintained at −70 degrees C. immediately after resection. Pathologic diagnosis was made by a surgical pathologist with experience in the diagnosis of sarcomas (BPR) according to WHO criteria (Fletcher et al., 2002). Leiomyomas were characterized by fascicles of spindle cells with elongated nuclei, fine chromatin and abundant eosinophilic cytoplasm. Leiomyosarcomas were characterized by fascicles of spindle cells with elongated nuclei, fine chromatin and abundant eosinophilic cytoplasm. However, in contrast to leiomyomas, leiomyosarcomas contained mitotic activity, cytologic pleomorphism and often contained necrosis. All leiomyomas and leiomyosarcomas were positive for smooth muscle actin, desmin and H-caldesmon by immunohistochemistry. Histologic grade of leiomyosarcomas was assigned by the French Federation of Cancer Centers Sarcoma Group grading system, which is based on degree of differentiation, mitotic activity, and necrosis (Guillou et al, 1997).

A portion of tumor specimens (12-patients altogether; 3 of each tumor grade) were fixed in 10% neutral buffered formalin then processed through into paraffin. Standard immunohistochemical analysis was used to determine versican levels in all the tumor grades.

Leica DMR upright fluorescent microscope equipped with Plan-Fluotar objectives (Germany) and RT Slider Spot camera was used to acquire all fluorescent images. A Leica DM2500 microscope with Leica N Plan objectives and a Insight model 14.2 Color-Mosaic camera (Diagnostic Instruments) was used for all light microscopy. The acquisition software was Advanced Spot (Diagnostics Instruments) Windows version 4.6.

The production of in vitro transcribed, versican-directed siRNA. To determine and select the siRNA that conferred the most effective knock-down of versican, we used in vitro transcribed small interfering RNAs (siRNAs) directed at the G1, beta-GAG, G3 regions of the versican molecule. To design the siRNAs, we used an on-line siRNA Template Design Tool (Ambion, 2130 Woodward St. Austin, Tex. 78744-1832 USA). The selected template oligonucleotides corresponding to the G1, beta-GAG, and G3 regions were then ordered from Sigma Genosys (The Woodlands, Tex.). We used the Silencer™ siRNA Construction Kit (Ambion Inc.; Austin, Tex.) to subsequently produce in vitro transcribed siRNAs. The annealed and purified siRNA products were quantified spectrophotometrically at 260 nm absorbance. Initially, to test the effectiveness of each individual siRNA, we applied 5 or 10 nM concentrations of each double stranded naked siRNA, complexed in GeneEraser™, an siRNA specific transfection reagent (Stratagene; La Jolla, Calif.), to a leiomyosarcoma cell line, SK-LMS-1, originally derived by Fogh and Trempe (1975). The SK-LMS-1 (ATCC; Manassas, Va.) cells are a human SMC cancer cell line that expresses abundant versican (Cattaruzza et al., 2004). $5 \times 10^5$ cells were plated into 6-well dishes (Cellstar, Greiner Bio-one; Longwood, Fla.). RNA was extracted 48 hours, post-transfection, using the TRIzol reagent (Invitrogen; Carlsbad, Calif.). Quantitative real time-PCR (Prism7000, Applied Biosystems; Foster City, Calif.) was performed to determine the level of versican message for each siRNA used versus control, which received only empty vector and/or transfection reagent.

The production of constitutively-expressed, versican-directed siRNA. Having determined which siRNA was the most effective at inhibiting versican, we ordered a 64-mer oligonucleotide pair (Sigma Genosys; The Woodlands, TX), annealed the sequences, and subcloned the corresponding cDNA:

```
                                        (SEQ ID NO: 1)
5'-GATCCCAATTCACCTTCGAGGAGGCTTCAAGAG-

AGCCTCCTCGAAGGTGAATTTTTTTGGAAA-3'
``` with its complementary 3' to 5' sequence and built-in BamH I and Hind III restriction site overhangsinto pSilencer-3.1-H1neo (Ambion; Austin, Tex.) plasmid vector containing the H1 RNA pal III promoter and neomycin-selection cassette. The H1 promoter is well characterized (Myslinski et al., 2001) and provides high levels of constitutive expression across a variety of cell types. We transfected the LMS cells using FuGene 6 per protocol (Roche; Basel, CH) and selected over 12-14 days using 600 ug/mL neomycin (G418; Gibco, Grand Island, N.Y.). The cells were split and individual cell islands were selected and isolated, then grown and cultured separately. These cell isolates having been selected, now represented only the transfected population of cells, and not heterogeneous population as the previous in vitro transcribed siRNA experiments. RNA from these stable cell lines was isolated using the same RNA extraction protocol, and qRT-PCR was then performed on siRNA expressing versus empty vector control clones. Assay-on-Demand (Applied Biosystems) probes were used to determine mRNA levels of versican. We normalized all our expression levels to either beta-actin or TATA-binding protein mRNA.

Extraction of purified versican. Versican was extracted from freshly acquired bovine or porcine aorta by first finely grinding the tissue directly into 4 M guanidine buffer (50 mM NaOAc, pH 5.8+ protease inhibitors 2 mM EDTA, 10 mM N-Ethylmaleimide (NEM), 25 mM 6-Amino-n-hexanoic acid (AHA), 5 mM Bezamidine-HCl, and 1 mM Phenylmethysulfonyl fluoride (PMSF)) using approximately 100-150 mls of the extraction buffer per gram of tissue. This mixture was extracted in the cold (4° C.) for 72-hrs., then filtered. The mixture was then dialyzed (12-14 kDa cutoff dialysis tubing) over 5-changes (20-liters) of $diH_2O$. The sample volume was then measured and solid urea was added and brought up to 6 M, plus 0.05 M NaOAc, 0.2 M NaCl and protease inhibitors. To uniformly extract all GAG-chain containing molecules, 80 mls of Diethylaminoethyl Sephacel (DEAE) was added, mixed for 30-minutes, then allowed to settle overnight at 4° C. The unbound "flow through" was removed, and the DEAE slurry containing the versican was decanted into conical centrifuge tubes. The DEAE was then washed in 4× volume excess 8M urea buffer with 0.25M NaCl five times, spinning down the DEAE between washes. The GAG-containing molecules were then eluted using 1M NaCl urea buffer. The sample was redialyzed through 5-changes of $diH_2O$ and the product was lyophilized (shell frozen) overnight. The sample was then resuspended in 3 mls of 8 M Urea Buffer (no Triton, no salt) and run on a Sepharose CL 4B (2×85 cm) column and collected in 6-minute fractions. Due to its size, versican for the most part, does not absorb to the column and will come off in the void fractions. In this manner the versican was isolated from other proteoglycans. The isolated versican was characterized as intact or degraded by running a fraction sample on an acrylamide gradient gel, and under chondroitinase digest conditions where the protein core integrity could be visualized. The purified versican was then used in subsequent proliferation and migration assays.

Protein expression levels of versican. The protein levels of versican were determined by taking media samples from versican siRNA cells and empty vector controls and running these samples though a DEAE binding column (allowing for proteoglycan specific extraction), followed by elution using higher salt, precipitation in urea buffer. The pelleted PGs were then subjected to chondroitin ABC lyase digestion (3-hrs at 37° C.) and electrophoresed overnight on a 4%-12% gradient SDS-PAGE gel. The bands that resulted, were then transferred to nitrocellulose, washed, and a pan-versican antibody (Vc rabbit anti-human polyclonal Ab was kind gift from Richard LeBaron, University of Texas at San Antonio) was applied to detect all versican isoforms.

Immunohistochemistry. For the immunohistochemical analysis, the primary antibody (rabbit polyclonal anti-human versican) and biotinylated-PG-link (b-PG), specific for HA, were titered to provide optimum contrast and specificity without saturation. Secondary antibody control (biotinylated goat anti-rabbit for versican) was performed in the presence of goat serum (species of the secondary) and absence of primary to assure low background and without false positive signal. Strepavidin-AP was used as secondary for HA staining. All primary and secondary antibodies and binding molecules were diluted in JM buffer. JM buffer consisted of one BupH Modified Dulbecco's PBS (Pierce #28374) packet in 500 ml ddH20 with 0.01% Tween 20, 0.1% saponin (Fluke; Sigma), sterile filtered, then 1% normal goat serum and 0.5% Tyramide Signal Amplification (TSA) block provided in the TSA Kit #22 (Alexa Fluor 488, Molecular Probes, Invitrogen; Carlsbad, Calif.) and sterile filtered again. DAPI (1 ug/ml) was added at the time of the secondary to visualize cell nuclei. The TSA Kit #22 was used per manufacturer directions to amplify the presence of epitope.

Growth and Migration. Cell growth and migration rates were determined as described previously (Lemire et al., 2002). Equal numbers of cells (50,000) were first plated (24-hours) in complete standard DMEM media, then grown in DMEM in the absence of serum for 72-hours. Then the cell media was changed (to complete DMEM, 10% FCS) and the cells were harvested over time and counted using a Coulter Z1 cell counter. Migration was determined by measurement of movement of cells (using ProView software; Media Cybernetics, Bethesda, Md.) into a cell-free zone created by scraping confluent cultures The change in area was measured at 0, 12- and 24-hours after the scrape was applied.

HA Enzyme-Linked Immunosorbent Assay. We used a competitive enzyme-linked immunosorbent assay (ELISA) in which the samples to be assayed were first mixed with biotinylated-PG-link and then added to an HA-coated microtiter plate, the final signal was inversely proportional to the level of HA. To isolate samples, medium from cultures was digested with papain (5 mg/ml) in 0.1 M Tris/acetate, 5 mM EDTA, 5 mM L-cysteine hydrochloride (HCl) at pH 7.3 for 18 h at 60° C. Following digestion, the papain was inactivated by heating to 100° C. for 20 min. For ELISA, we used a modification of that previously described (Underhill et al., 1993). Briefly, on day 1, 75 µl of standards and samples were incubated with 75 µl b-PG (5 µg/ml) overnight. Also on day 1, 100 µl of HA-BSA preparation was added to each well of a Nunc-Immuno 96-well plate (Nalge Nunc International) and incubated for 1 hour at room temperature. Plates were washed ×3 in PBS using a Denley Wellwash 4 mechanical plate washer. Then, 200 µl of 10% calf serum (CS) in PBS was added and incubated overnight. On day 2, plates were washed as before and then 60 µl of the incubated b-PG/HA standards and samples were added to duplicate wells and incubated for 2 hours at room temperature. Plates were washed as before and then 60 µl of streptavidin-labeled peroxidase (2 µg/ml) was added to each well and incubated for 30 min at room temperature. Plates were washed as before and then 60 µl of 2,2' azinobis 3-ethyl-benzthiozoline sulfonic acid (AEBT-SA) in 0.1 M sodium citrate pH 4.2 was added. The resulting absorbances were measured at 405/570 nm on a OPTImax microplate reader (Molecular Devices, Sunnyvale, Calif.) using SOFTmax PRO (version 4.3) software (Molecular Devices). Readings at 570 nm were subtracted from those at 405 nm to account for plate imperfections.

RNA Isolation. Total RNA was isolated as previously described (Chomczynski, 1993). In brief, cells were cultured in 60 mm dishes, the medium removed, and the plates placed on ice. Then 1.5 ml of cold TRIzol reagent (Invitrogen Life Technologies, Carlsbad, Calif.) was added and the cell layers incubated on ice for 5 min. Then 300 µl of chloroform/isoamyl alcohol (24:1) was added and the samples mixed and then centrifuged at 13,000 rpm for 20 min. A total of 700 µl of the aqueous phase was mixed with an equal volume of isopropanol, incubated at −70° C. overnight, centrifuged at 13,000 rpm for 20 min before washing once in 100 µl of 75% ethanol then resuspended in 20 µl of sterile water. Finally, deoxyribonuclease (DNase) was added at 0.02 U/µl and the samples incubated at 37° C. for 15 min. The RNA was purified by adding 100 µl of acid (pH 4.5) phenol:chloroform:isoamyl alcohol (25:24:1) to an equal volume of DNase-treated sample, mixed and centrifuged. Samples were extracted once again in chloroform:isoamyl alcohol (24:1) and precipitated using 80 µl RNA sample, 8 µl 3 M sodium acetate, and 200 µl of ethanol. Samples were then washed in 100 µl of 70% ethanol and resuspended in sterile water. Total RNA was quantified by measuring the absorbance at 260 and 280 nm in a Beckman DU640 spectrophotometer (Fullerton, Calif.). The purity of the samples was always $A_{260}/A_{280}>1.8$.

Reverse Transcriptase-Polymerase Chain Reaction. Expression of versican and the three isoforms of HAS was examined by reverse transcriptase-polymerase chain reaction (RT-PCR). Synthesis of single-strand cDNA was performed in 50 µl reactions (reagents were purchased from Promega unless stated otherwise) using 1 µg total RNA, 2 µl oligo-dT (Ambion, Austin, Tex.), 2.5 µl RNase inhibitor (40 U/µl), 5 µl deoxynucleotide triphosphates (dNTP), 10 µl 5× Improm-II buffer, 12 µl MgCl$_2$ (25 mM), and 2.5 µl Improm-II reverse transcriptase per RNA sample. Annealing was performed at 25° C. for 5 min and cDNA single-strand synthesis was at 42° C. for 90 min.

Conditions for PCR amplification were optimized for MgCl$_2$ concentration and temperature using a PTC-200 peltier thermal cycler (MJ Research, Waltham, Mass.). PCR reactions were performed using 1 µl single-strand cDNA product, 250 µM dNTP, 2 µl 10× AmpliTaq Gold buffer, 5 pM of each primer, 0.75 U AmpliTaq Gold enzyme (Applied Biosystems, Foster City, Calif.), and MgCl$_2$ (1.6 mM Versican, 1.6 mM HAS-1, 1.6 mM HAS-2, 2.2 mM HAS-3, and 1.6 mM GAPDH). After a 10 min initial enzyme activation step at 95° C. for the AmpliTaq Gold, samples were denatured for 1 min at 95° C., annealed at 59.5° C. for 1 min, and extended at 72° C. for 1 min.

Animal model experiments. We used a well established tumor cell growth model (Horiuchi et al., 2000) combined with the clonal populations of the human uterine tumor cells, SK-LMS-1, described above. Nine immunocompromised BALB/c nude mice (Charles River Laboratories; Wilmington, Mass.) each received 2×10$^6$ versican knockdown cells on one dorsal flank subcutaneously, and the same 9 received, 2×10$^6$ empty vector control cells on the opposite dorsal flank. The mice were observed every day after the initial injection, and tumor volumes were measured from the living animals. At the end of the study, the animals were euthanized and the tumors were excised for further histological analyses to determine versican and HA expression levels, and tumor cell mitotic index. This study was approved by our institutional Animal Care and Use Committee, and care and use of the experimental animals was performed in full accordance with the Animal Welfare Act.

Tumor volume measurements and monitoring. The mice were observed every day after treatment, and tumor volumes were measured every day beginning on the 2$^{nd}$ day post injection to negate any measurement of edema or fluid from the injection bolus. The volume of the tumor (V) was calculated on the basis of 3 mutually orthogonal measurements (X, Y and Z) of the tumor nodule made using a high precision (accurate to 0.001 mm) digital vernier caliper. As in a previous report, the formula V=XYZ π/6 was used to calculate tumor volume (Hyacinthe et al., 1999). The number of tumors used for volume measurements in each group was 6.

Histology. After 21-days of tumor growth, the mice were sacrificed. The tumors were excised and fixed in 10% neutral buffered formalin for 24 hrs, then processed through to paraffin. 5 µm sections were used for hematoxylin and eosin staining and all immunohistochemistry staining. The total number of evident mitotic figures (MFs) was counted in 10 randomly selected high-power fields (HPFs; 400×) per section and expressed as a mitotic index (MI). Mitotic figures were counted in 5 sections or more from each tumor and compared for MI values. The number of tumors used for histologic evaluation and mitotic counting was 3 for each group. We also looked for histologic changes in the skin overlying the tumor.

Statistical analysis. Two-tailed Student's t-test was used to compare tumor volumes among the 2 study groups. The data are presented as the mean±SE. Students t-test was used to determine significance all other analyses. These statistical analyses were performed using MS-Excel v.7.0 (Microsoft, Redmond, Wash.). Differences were considered significant when p<0.05.

Results

In Vivo Leiomyosarcoma Lesional Tissues Indicate a Significant Upregulation of Versican.

Samples taken from 9 patients identified with grades 1-3 LMS tumors when probed immunohistochemically for versican, indicated strong versican component in lesion connective tissue (FIG. 1-1). Tumor grades 1 and 2 showed the most intense versican staining, and areas of high versican expression corresponded to areas of the greatest cellularity in the lower grade tumors. Grade 3 LMS tumors still displayed increased versican staining over the benign leiomyoma, but were far less cellular in core areas and were hyaline and diffusely stained for versican. Histologically, the tumors grew in interlacing bundles of smooth-muscle cells displaying multifocal, moderate to severe cytologic atypia and a mitotic index of greater than 10 mitotic figures per 10 high power fields. Furthermore, Northern blot data from homogenized LMS tissue indicate significantly higher versican mRNA levels versus adjacent normal myometrial controls (FIG. 1-1E).

Achieving effective knock down of versican. Using qRT-PCR as our read out and in vitro transcribed siRNA specifically directed and spaced along the length of versican mRNA, we determined that 5'-G1-directed siRNA was the most effective at inhibiting versican (55% knock-down vs. 22% or less for the other domain regions). Subsequently, we successfully subcloned the corresponding siRNA cDNA into pSilencer-3.1-H1neo plasmid expression vector with its neomycin selection cassette and confirmed by sequencing the proper orientation and sequence of the insert. In this manner we successfully produced stable clones with constitutive knock-down of versican.

Consequences of constitutively down-regulating versican by siRNA. By qRT-PCR we found that we were able to achieve as much as an 85% knock-down in the versican mRNA (FIG. 1-2A), and 95% in terms of the protein levels by Western blot (FIG. 2B). These results were supported by immunohistochemical analysis which showed that the versican levels were also significantly downregulated (FIG. 1-2C). The results indicated that the cells in which the versican levels had been reduced by versican directed siRNA, proliferated and migrated at dramatically reduced rates (FIGS. 1-3 and 1-5). Thymidine incorporation of LMS cells showed a greater than 3.5-fold higher incorporation rate than the LMS cells in which versican was being suppressed. This was observed for all the clones tested (n=7). The cell growth over time was also significantly slower in the versican siRNA cells (FIG. 1-3B). What is more, the trypsinsization time for complete cell removal from cell culture plastic, changed with changing versican levels. The time for cells to be removed from cell culture plastic was approximately 10× longer for the versican siRNA cells versus the empty vector control LMS cells (FIG. 1-4). When versican was added—back to determine its effect on cell proliferation, the cells not only proliferated more rapidly (FIG. 1-3C), but were less adhesive in a dose dependent manner (FIG. 1-4B).

Furthermore, it was noted that these LMS cells not only produce an abundance of versican, but the media of these cells was highly viscous. We hypothesized that this was the result of a high levels of hyaluronan (HA). In subsequent, ELISA and RT-PCR experiments, we observed a corresponding decrease in specific hyaluronan synthase (HAS) expression and HA production levels in versican directed siRNA clones (FIG. 1-6). HAS-1 primer failed to produce a band, even after 40-cycles, and therefore is not shown. In any case, this suggest a direct link between versican expression, and HAS and HA expression. Having determined this, we asked question was HA or versican driving the cell proliferation rate? We determined that the exogenous addition of large molecular weight HA did not have the same effect as the exogenous addition of versican (FIG. 1-7). There did appear to exist a synergistic effect, however, between HA and versican as the proliferation rate of the versican alone was lower in comparison to the combination of HA and versican (p<0.0006).

Tumor induction in nude mice. Having modified these cells in such a way that the ECM molecule versican had been knocked down, and having observed that the knock down of versican expression in LMS cells was accompanied by slower rates of proliferation and migration, and increased cell adhesion to the culture dish, we, therefore, asked the question, is versican synthesis necessary for LMS tumor formation? When nude mice were injected subcutaneously with LMS cells constitutively expressing versican siRNA and non-modulated control LMS cells, the immunohistochemical analysis for versican and HA revealed that the empty vector control LMS tumors continued to express a high levels of versican and HA (FIG. 1-8) while the versican siRNA tumors had very low expression levels of versican and HA (FIG. 1-8, panels B and D) and were smaller (FIG. 1-9A). Furthermore, the tumor growth continued unpreturbed in the control LMS cells, while the same cells now modified by versican directed siRNA, failed to thrive and displayed limited growth (FIG. 1-9A). What is more, mitotic index analyses showed 3-4 fold lower cell division kinetics for the versican siRNA cells (FIG. 1-9B).

Discussion

In this study, we describe the observed increase in versican expression levels in grades 1-3 leiomyosarcoma over benign leiomyoma. We found that areas of high versican expression levels corresponded to areas of increased cellularity for the lower grade tumors. The observation of increased versican levels in LMS tumors has also been observed in breast and prostate cancers (Cattaruzza and Perris, 2005; Cattaruzza et al., 2004; Cattaruzza et al., 2002) and is associated with high metastatic potential and or poor prognosis in patients with cervical cancer (Kodama et al., 2007); laryngeal (Skandalis et al., 2006), testicular (Labropoulou et al., 2006), and colorectal cancers (Tsara et al., 2002; Theocharis, 2002).

When we knocked-down versican, we found a dramatic change in cell phenotype of the LMS smooth muscle cells. In all cases, $^3$H-thymidine incorporation was lower, adhesion to cell culture plastic increased, cell morphology changed, and cell migration and proliferation was reduced. These cells were also similar in their phenotype to smooth muscle cells induced to overexpress the GAG-less V3-isoform of versican in regard to their low proliferative and migratory rates, as well and tight adherence to the plastic cell culture dish (Lemire et al., 2002).

Moreover, versican's binding partner HA, both in its synthesizing enzyme and its secreted level was also reduced. This study for the first time identifies versican in its modulation, and resulting cell phenotypic alteration, impacting the HAS enzyme copy number and HA synthesis. What aspect of cell phenotypic change is leading to changes in HAS and HA remains to be determined. HAS enzyme being plasma membrane localized, suggests that alteration in the cell shape or cell surface tension imparted by the down-regulation of versican is controlling HA synthesis and or HAS expression. Another possibility is that versican is serving as HA's "ECM receptor" whereby when the versican "sink" is lost, HA secretion is not facilitated due to lack of interaction with versican, and HA levels decrease.

The discovery of cell surface HA binding receptors CD44 and RHAMM (Aruffo et al., 1990; Goldstein et al., 1989) first revealed the potential role for HA in directly regulating cell motility, invasion, and proliferation. None the less, because CD44 binds multiple ligands and participates in growth factor signaling (Bourguignon et al., 2007), the role for HA in these CD44-regulated processes remains, for the most part, to be determined and is not addressed in this study.

However, our in vitro studies suggest that versican, and not HA, is what drives cell proliferation. Dr. Burton Yang's group in Toronto (Wu et al., 2001 and 2004; Zheng et al., 2004; Sheng et al., 2005) have provided some evidence to suggest how versican is potentially increasing cell proliferation. When Zheng et al., (2004), overexpressed the G3 domain of versican in U87 astrocytoma cells, they found that G3-transfected cells formed larger tumors than did control vector-transfected cells. The presence of G3 in cell cultures induced focal adhesion kinase phosphorylation, increased cell spreading and enhanced adhesion (Wu et al., 2004). Much of these effects are attributed to modulation of cell signaling through the EGF-receptor via versican G3 interactions.

For LMS tumors, a mitotic index of 10 MFs/10 high power fields together with diffuse cytologic atypia and coagulative tumor cell necrosis are features usually associated with metastases (Jones M W and Norris H J, 1995; Robboy S J et al., 1990; Perrone T and Dehner L P, 1988). Here we observed on average, 31.6-mitotic figures per 10 400× fields for the control LMS tumors, and 9.2-mitotic figures per 10-400× fields for the versican siRNA tumors. This indicates that versican is indeed playing an active role in the pathology of LMS tumors. The reduction in migratory potential (reduced cell migration and greater adhesion to substrate) combined with reduced LMS cell proliferation, tumor size, and mitotic index as a result of reduced versican expression, identifies the ECM proteoglycan versican as a potential point of control for LMS.

Example 2

Use of Versican V3 and Versican Antisense Genes to Engineer Elastin-Rich and Lipid-Resistant Neointimae in Balloon Damaged Arteries We have shown previously that over-expression of the versican variant V3 stimulates the synthesis of tropoelastin and the assembly of elastic fibers, both in vitro and in vivo (Merrilees M J, et al., *Circulation Research* 2002; 90:481-487). Over-expression of an antisense sequence to versican similarly stimulates elastogenesis (Huang, R. et al., *Circulation Research* 2006; 98: 370-377.). In both systems the increase in elastic fiber deposition is accompanied by a decrease in pericellular versican, an inhibitor of fiber assembly. Versican has also been shown to bind low density lipoprotein (LDL) and it has been argued that the trapping of LDL in the arterial wall by versican or other similar matrix proteoglycans is the primary event in atherosclerosis (K. Williams and I. Tabas, *Arterioscler Thromb Vasc Biol* 1995;15:551-561; G. Camejo et al., *Atherosclerosis* 1998; 139:205-222; T. Wight and M. Merrilees M J. *Circulation Research* 2004; 94:1158-67.).

Figures 1, 2, 3, 3A:
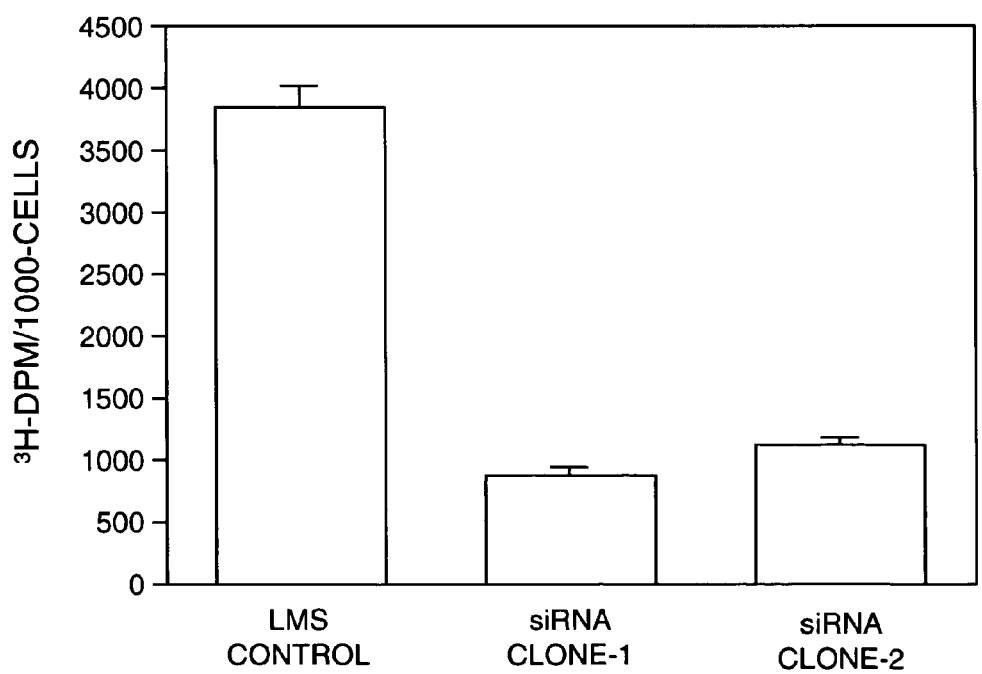

In order to determine if over-expression of V3 or versican antisense can stimulate an elastin-rich and a lipid-resistant neointima we carried out balloon catheter angioplasty of rabbit carotid arteries followed by seeding of smooth muscle cells transduced with vector alone, V3, and versican antisense in accordance with known procedures (FIG. 2-1). Cells (~50,000/vessel) were allowed to settle and attach to the endothelial-denuded surface for 15 minutes before re-establishing blood flood. Animals were maintained on a normal chow diet for 4 weeks prior to cholesterol feeding for a further 4 weeks FIGS. 2-2 and 2-3). At the end of the experiment, vessels were perfusion-fixed under pressure and collected for analysis (FIG. 2-4). Frozen sections were cut and stained for lipid (oil red O), elastin (orcein) and versican (immunostaining). Intimal thickness was determined by morphometry, and lipid content by stain intensity using NIH Image. Elastin was also detected by autofluorescence.

The results show that both the V3 and the versican antisense treated animals had thinner-intimas with reduced lipid deposition (FIGS. 2-5 and 2-6) and increased elastic fiber formation compared with control vessels (FIGS. 2-7 to 2-11).

These findings demonstrate that it is possible to engineer a new lining in a blood vessel that is both elastin-rich and lipid resistant using a single treatment with a single agent.

Example 3

Inhibition of Monocyte Retention by Interference with ECM Formation in Poly I:C-Treated Cells Viruses are known to exacerbate asthma and other lung diseases. Previous studies have shown that the viral mimetic, polyinosinic:polycytidylic acid (poly I:C) stimulates intestinal smooth muscle cells to produce an extracellular matrix (ECM) enriched in hyaluronan that binds monocytes.

Antibodies to versican interfered with monocyte adhesion to the extracellular matrix (ECM), indicating a key role for this ECM component. These studies indicate an important role for versican in viral-induced infiltration of inflammatory leukocytes. Antibodies to versican blocked the production of a monocyte-retaining ECM.

Figures 1, 2, 3, 3B:
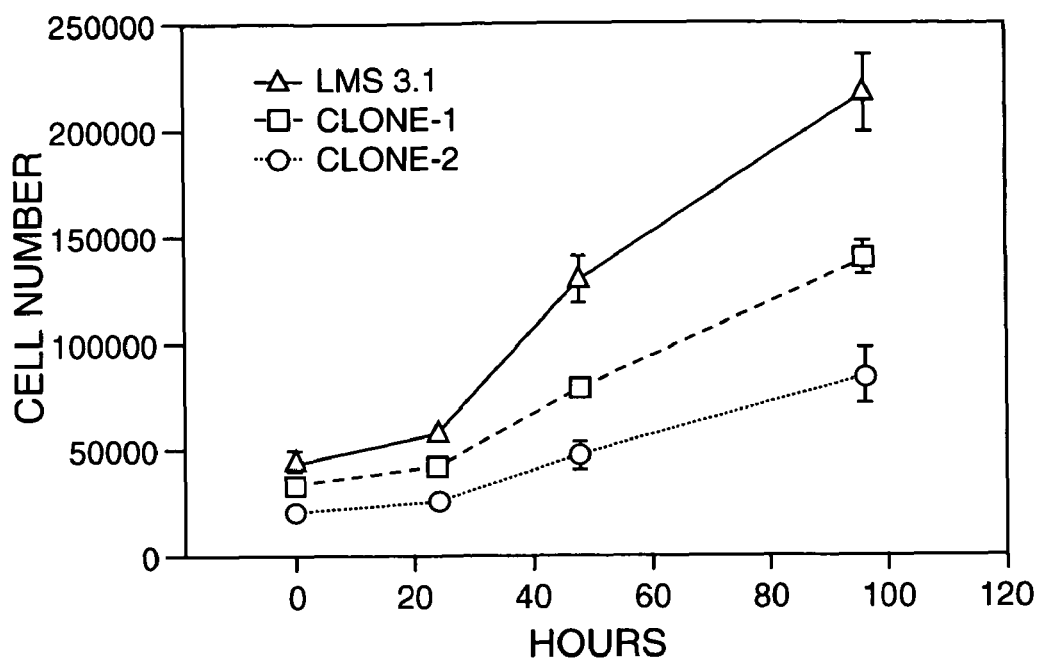
Figures 1, 2, 3, 3C:
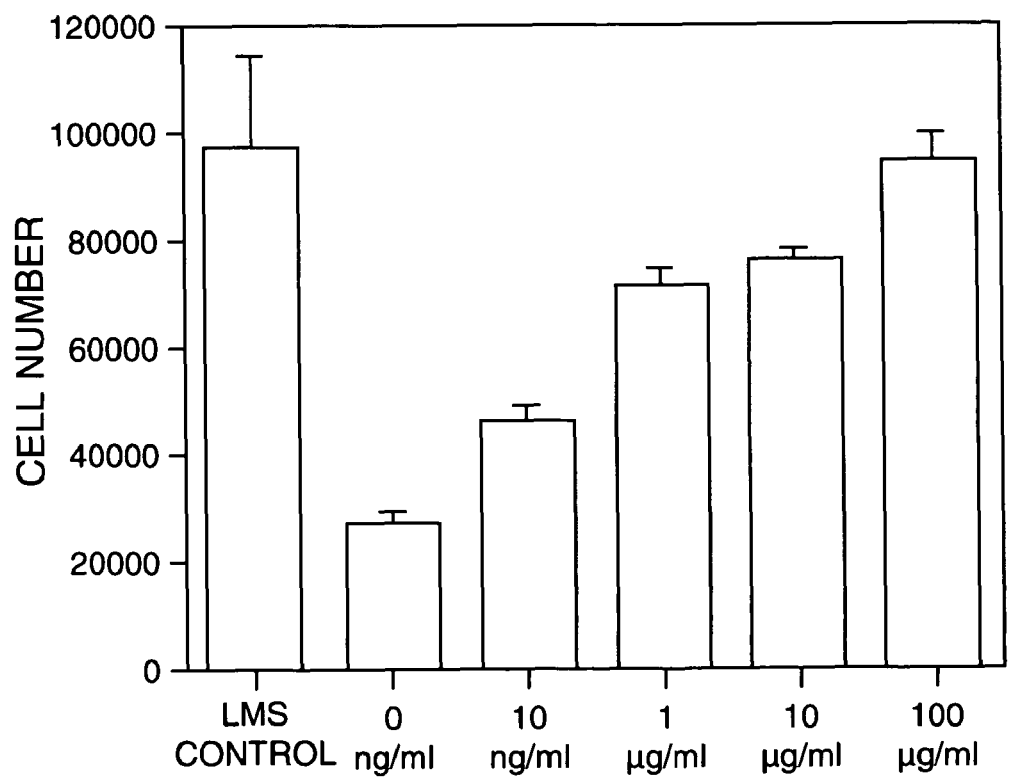
Figures 1, 2, 3, 4, 4A:
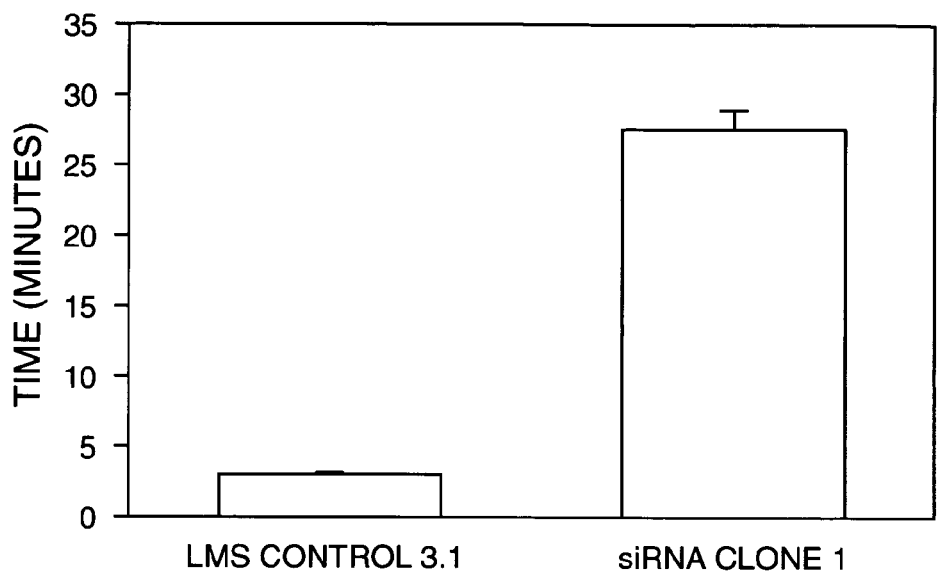
Figures 1, 2, 3, 4, 4B:
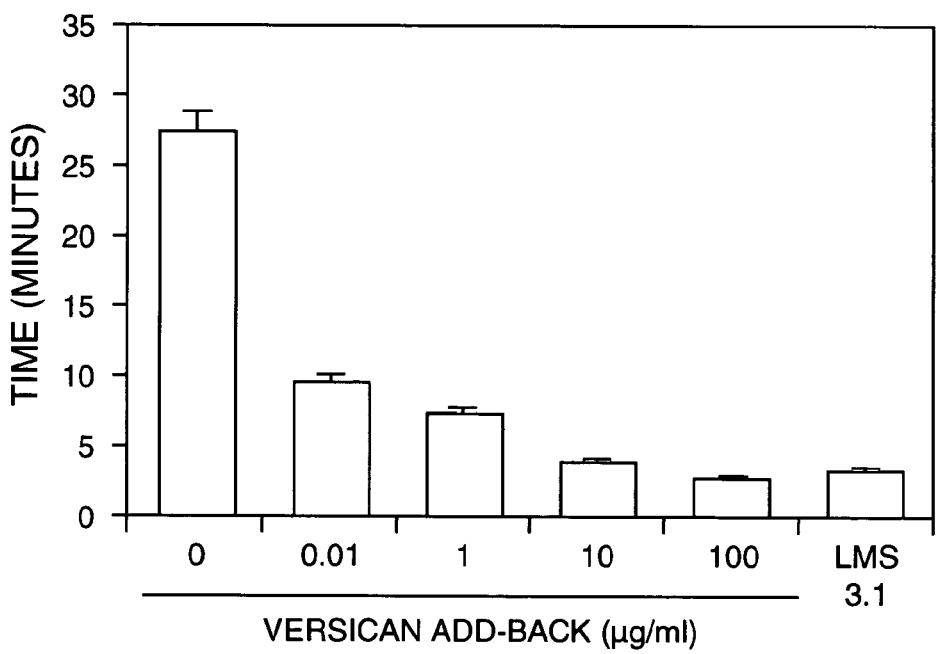
Figures 1, 2, 3, 4, 5, 5A:
Figures 1, 2, 3, 4, 5, 5B:
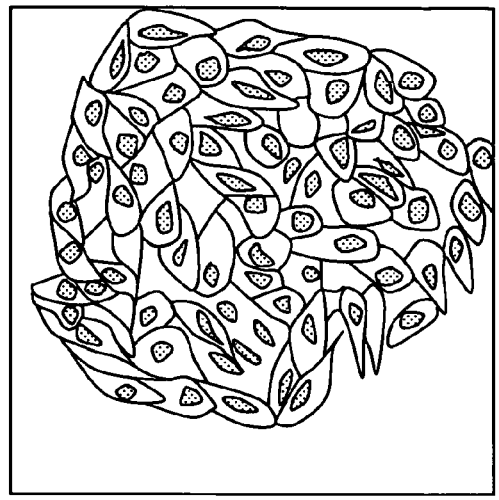
Figures 1, 2, 3, 4, 5, 5C:
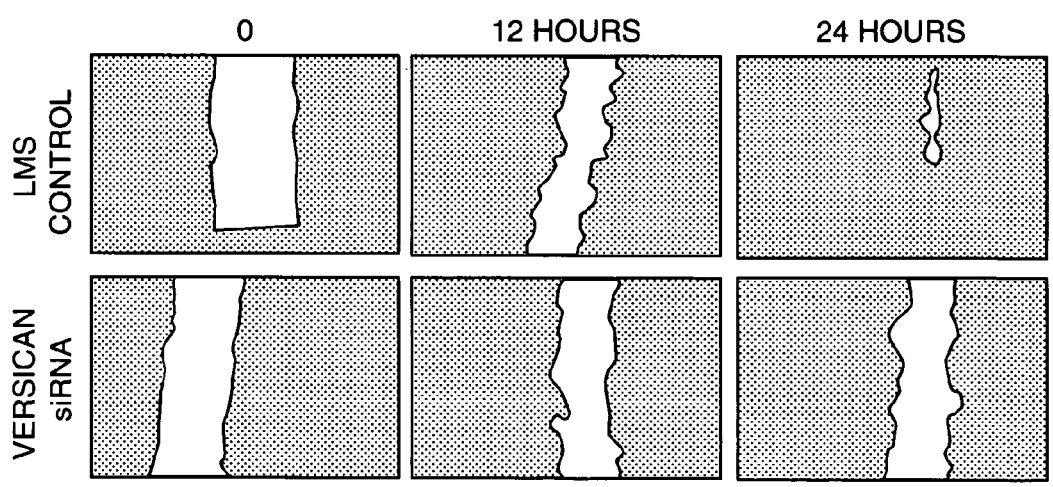
Figures 1, 2, 3, 4, 5, 5D:
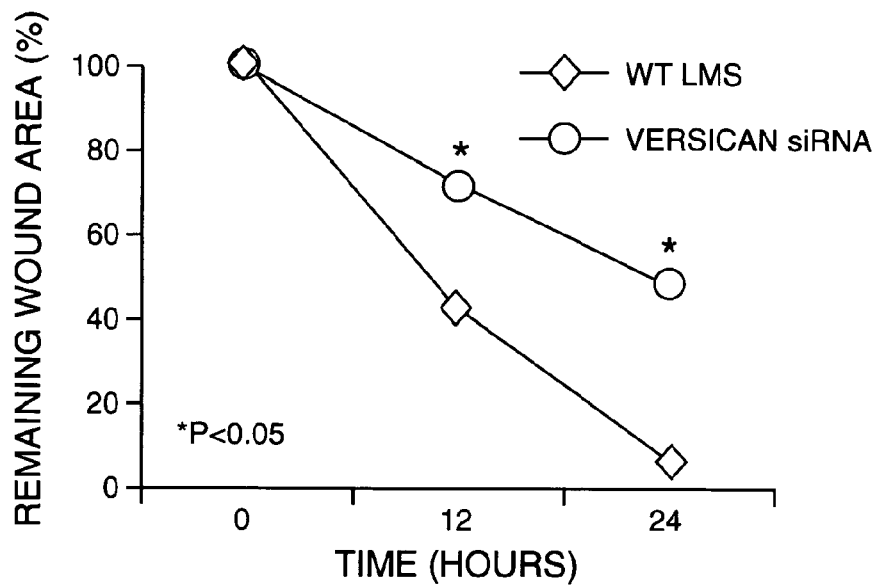
Figures 1, 2, 3, 4, 5, 6, 6A:
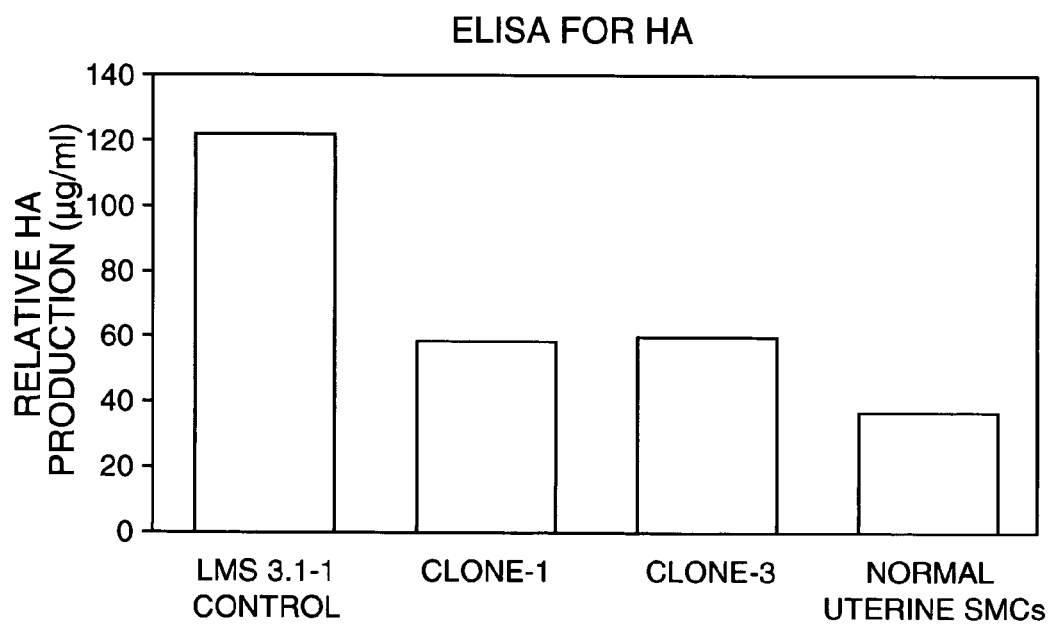
Figures 1, 2, 3, 4, 5, 6, 6B:
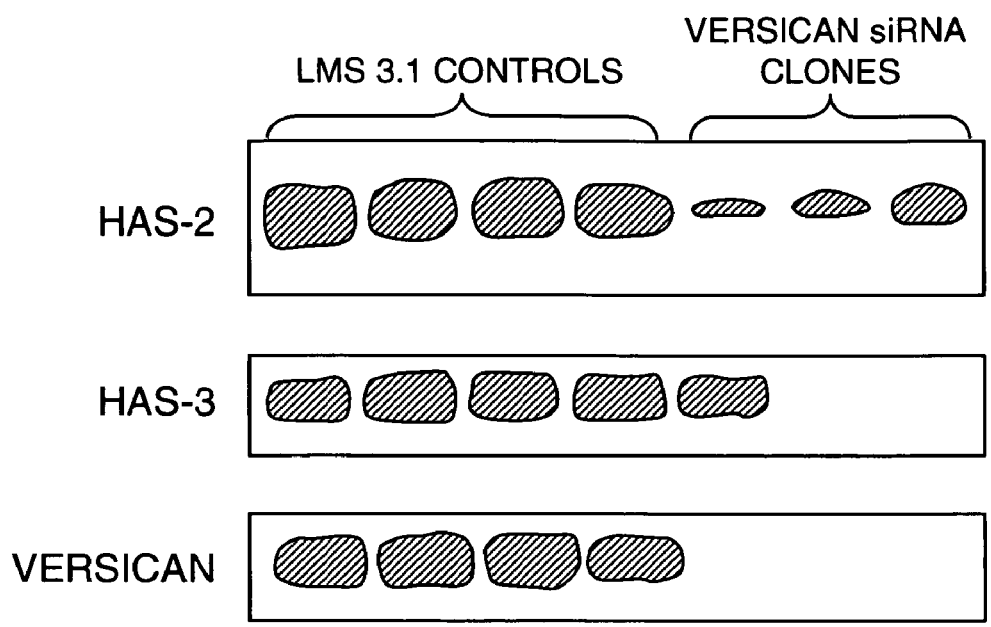
Figures 1, 2, 3, 4, 5, 6, 6C:
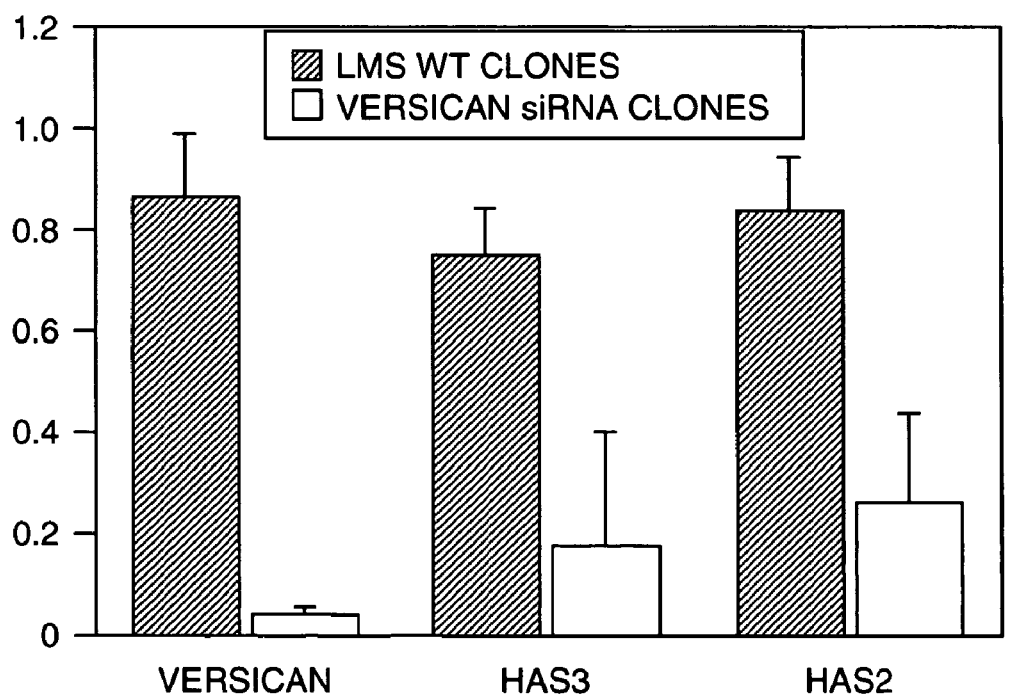
Figures 1, 2, 3, 4, 5, 6, 7:
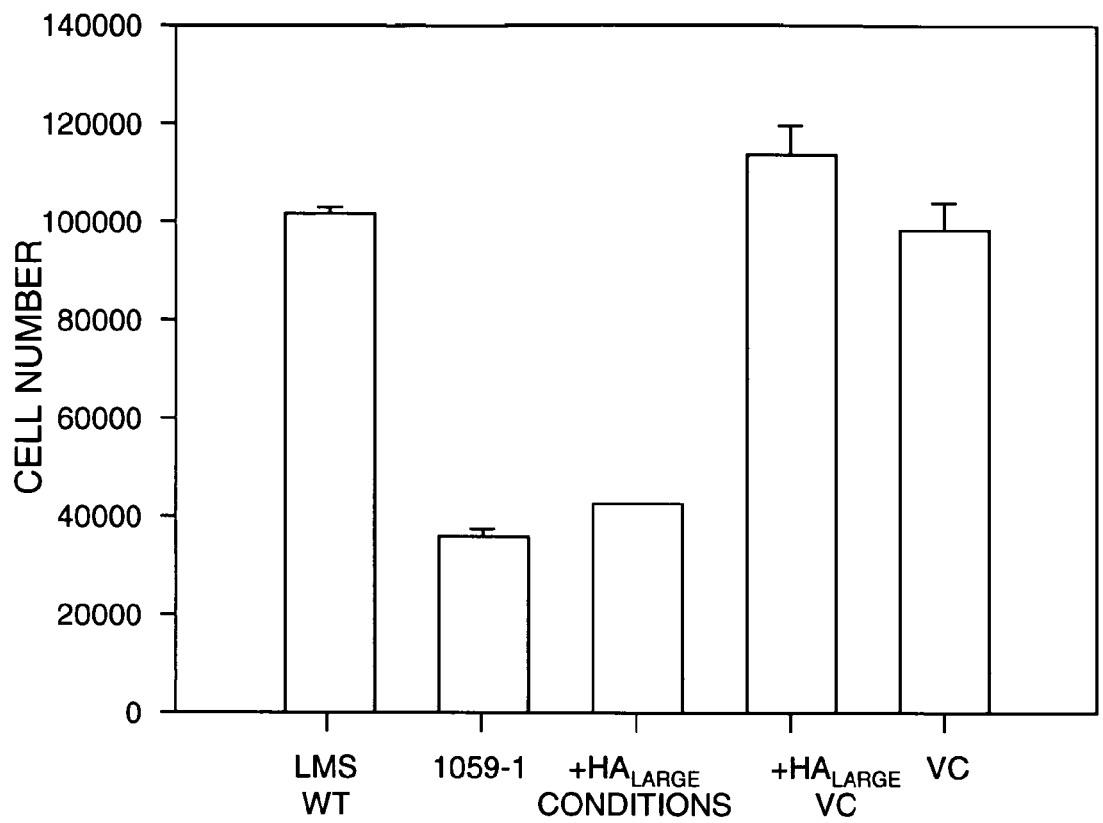
Figures 1, 2, 3, 4, 5, 6, 7, 8, 8A:
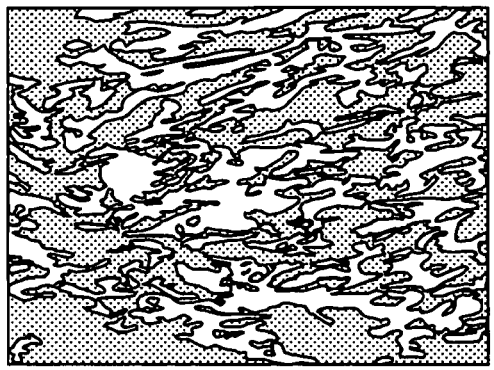
Figures 1, 2, 3, 4, 5, 6, 7, 8, 8B:
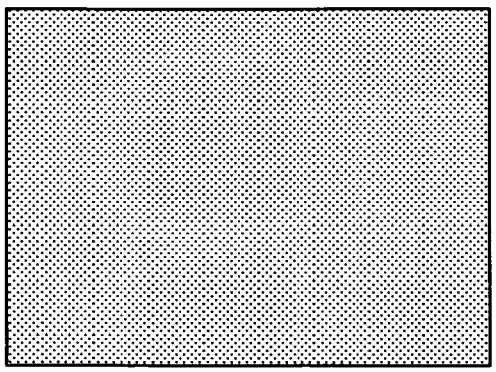
Figures 1, 2, 3, 4, 5, 6, 7, 8, 8C:
Figures 1, 2, 3, 4, 5, 6, 7, 8, 8D:
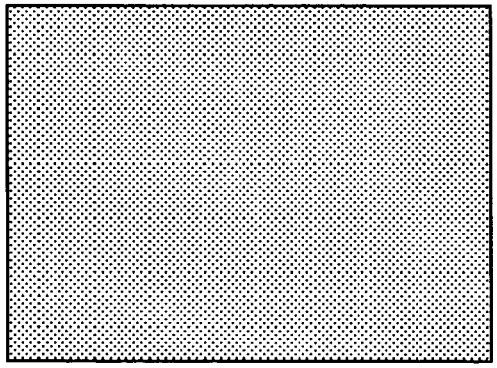
Figures 1, 2, 3, 4, 5, 6, 7, 8, 9, 9A:
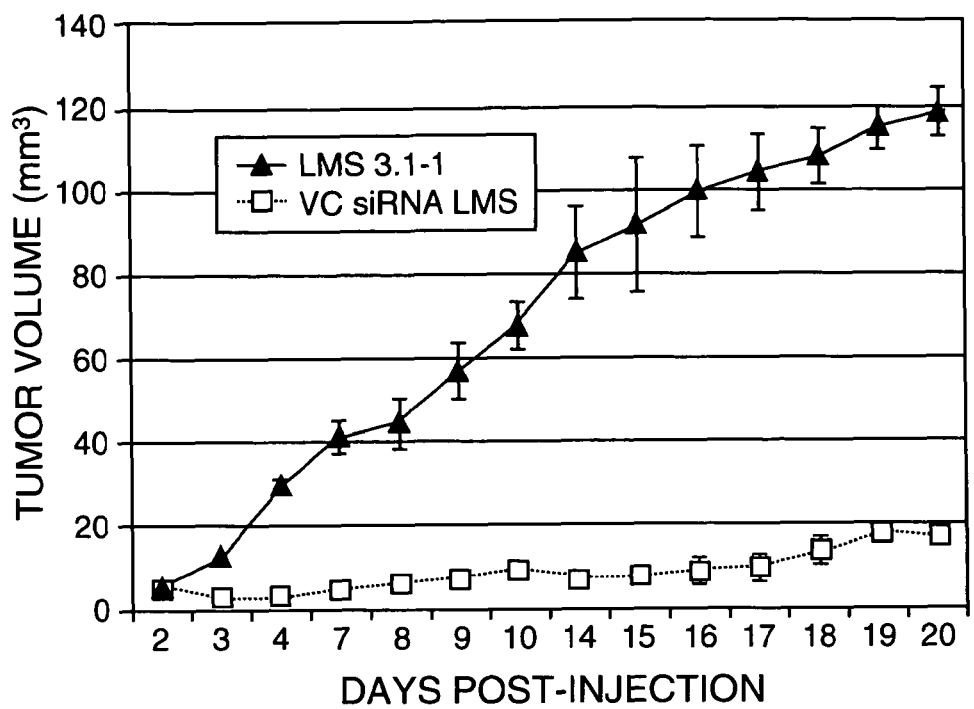
Figures 1, 2, 3, 4, 5, 6, 7, 8, 9, 9B:
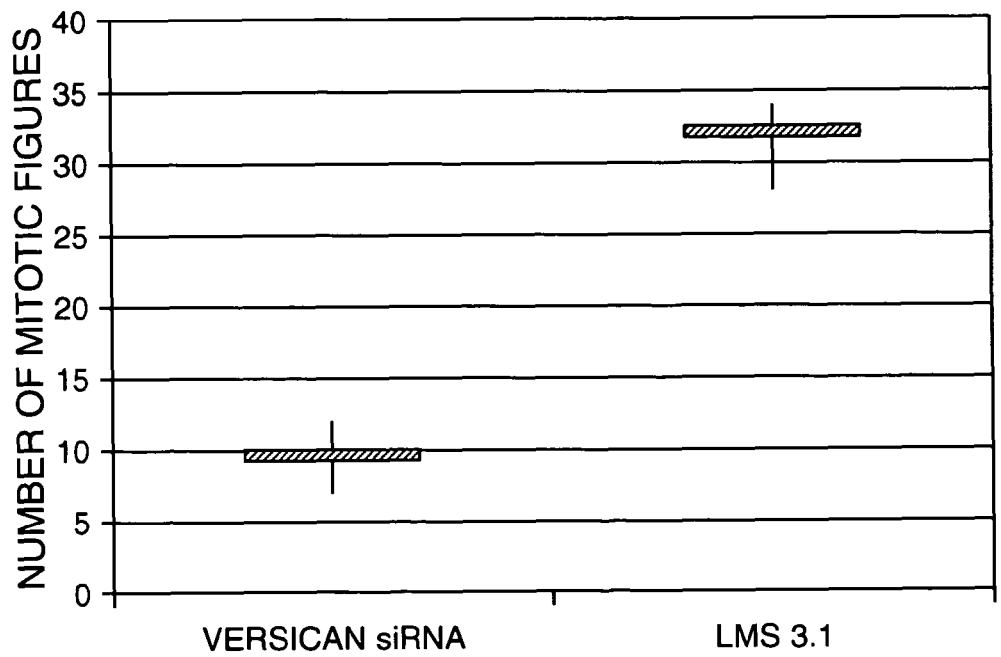
Figures 1, 2:
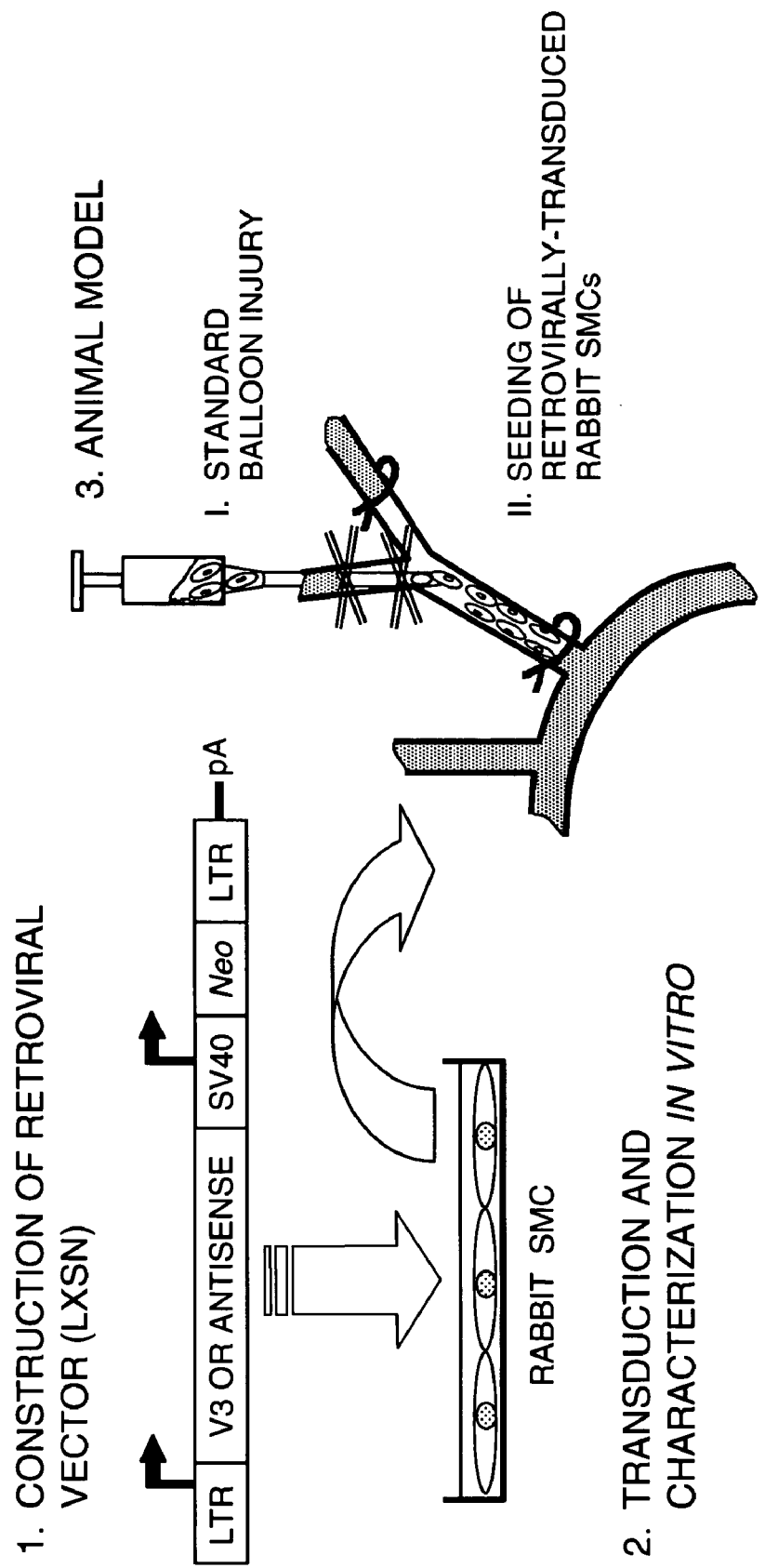
Figure 2:
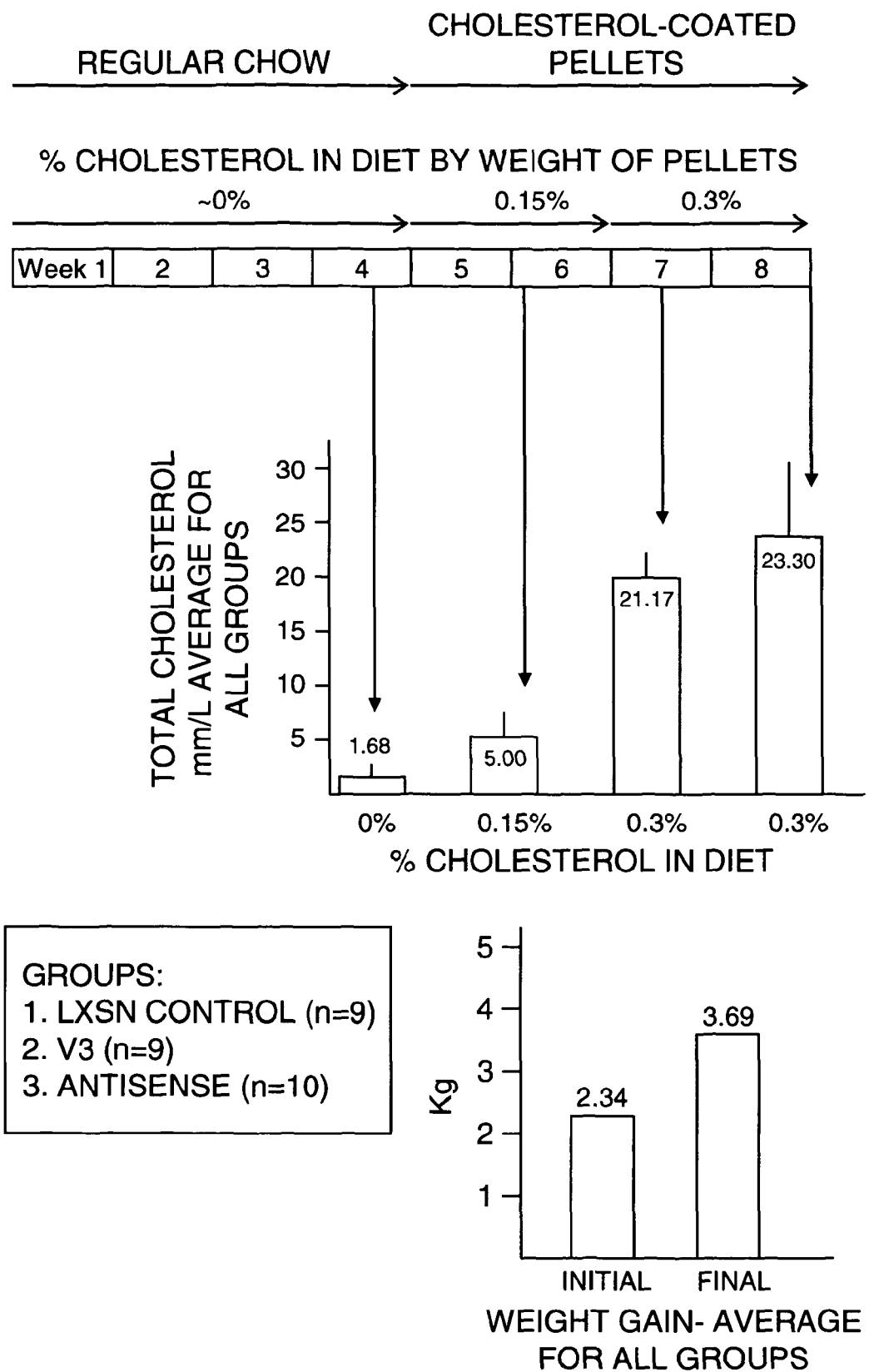
Figures 2, 3:
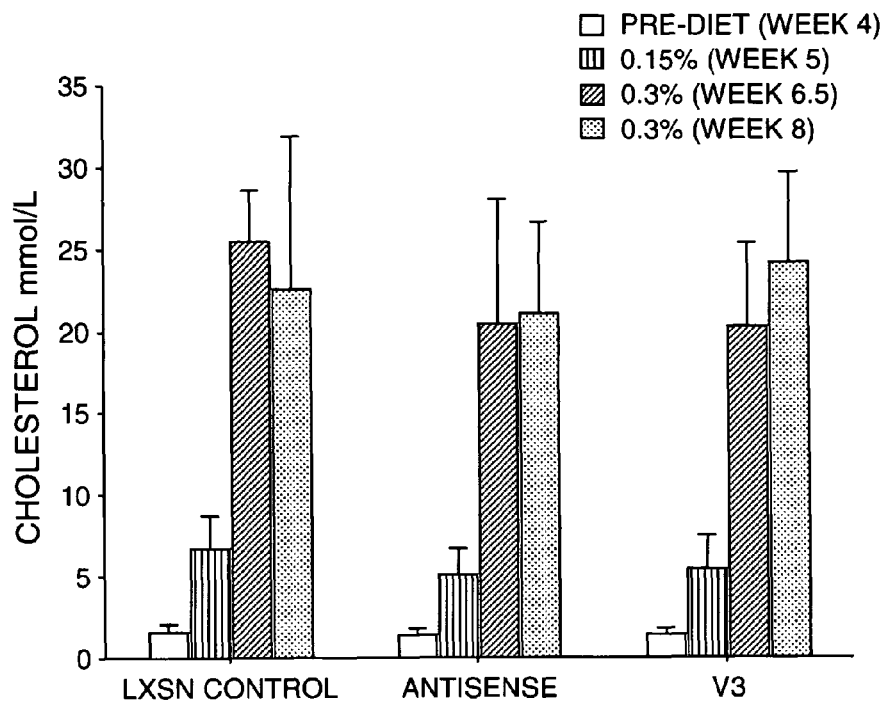
Figures 2, 3, 4:
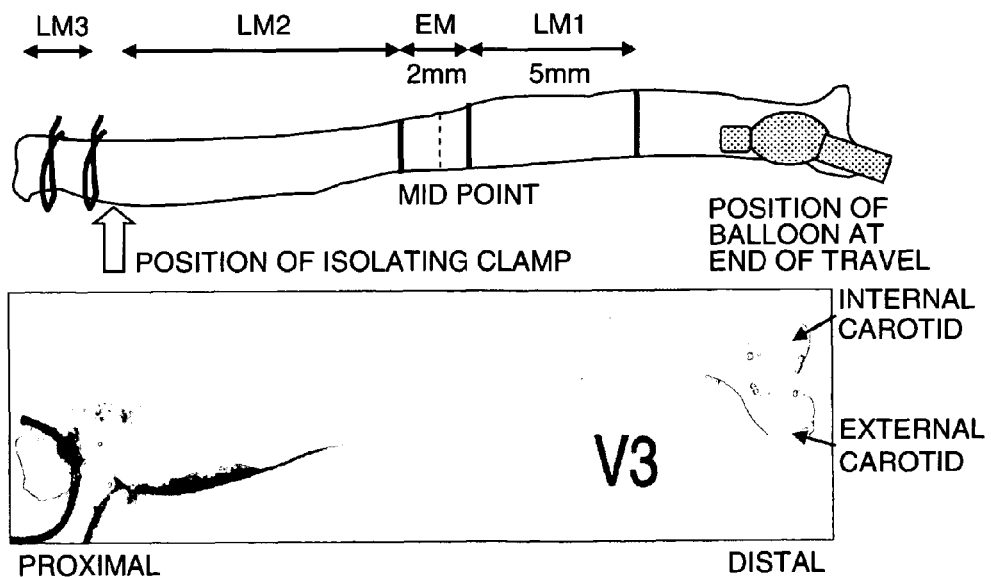
Figures 2, 3, 4, 5, 6:
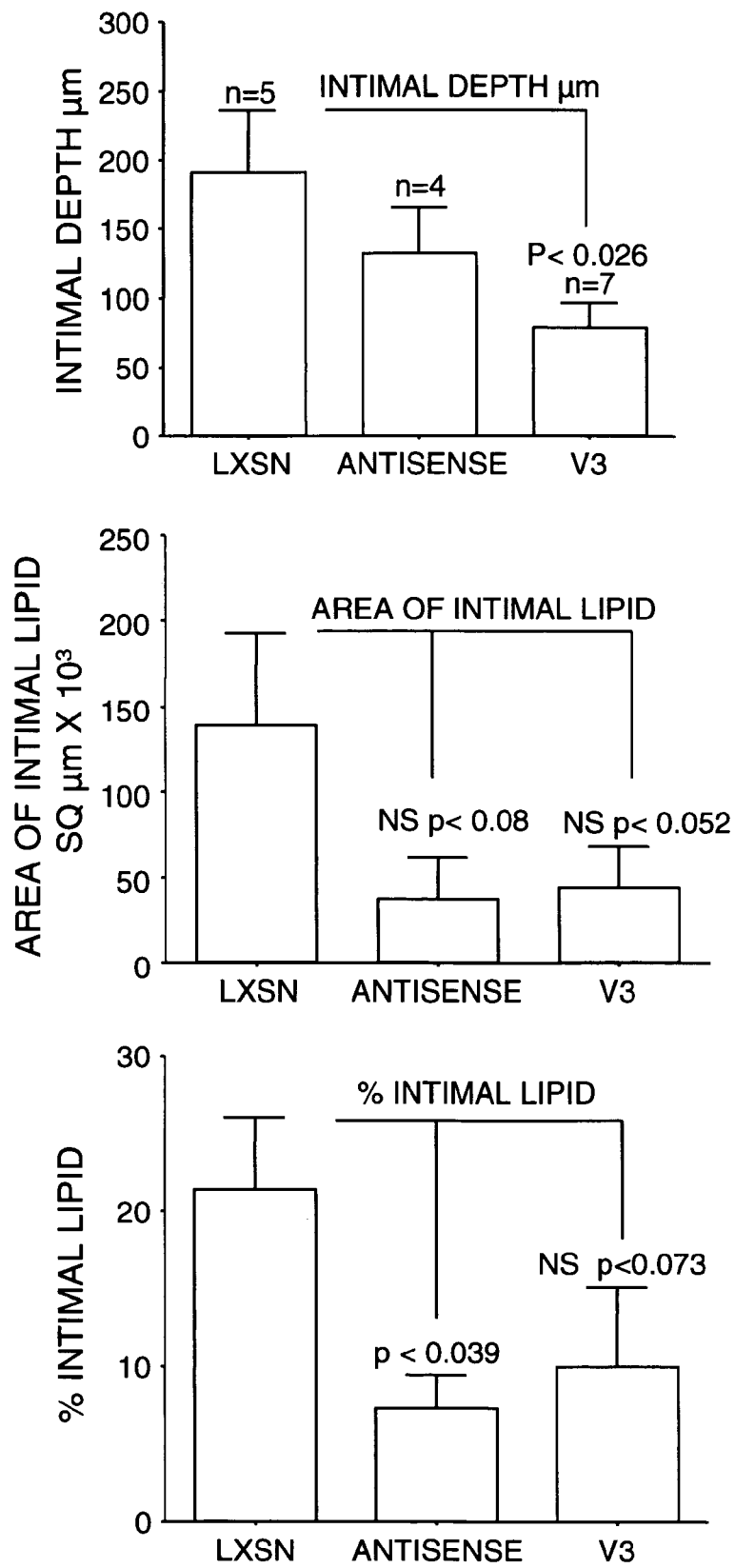
Figures 2, 3, 4, 5, 6, 7:
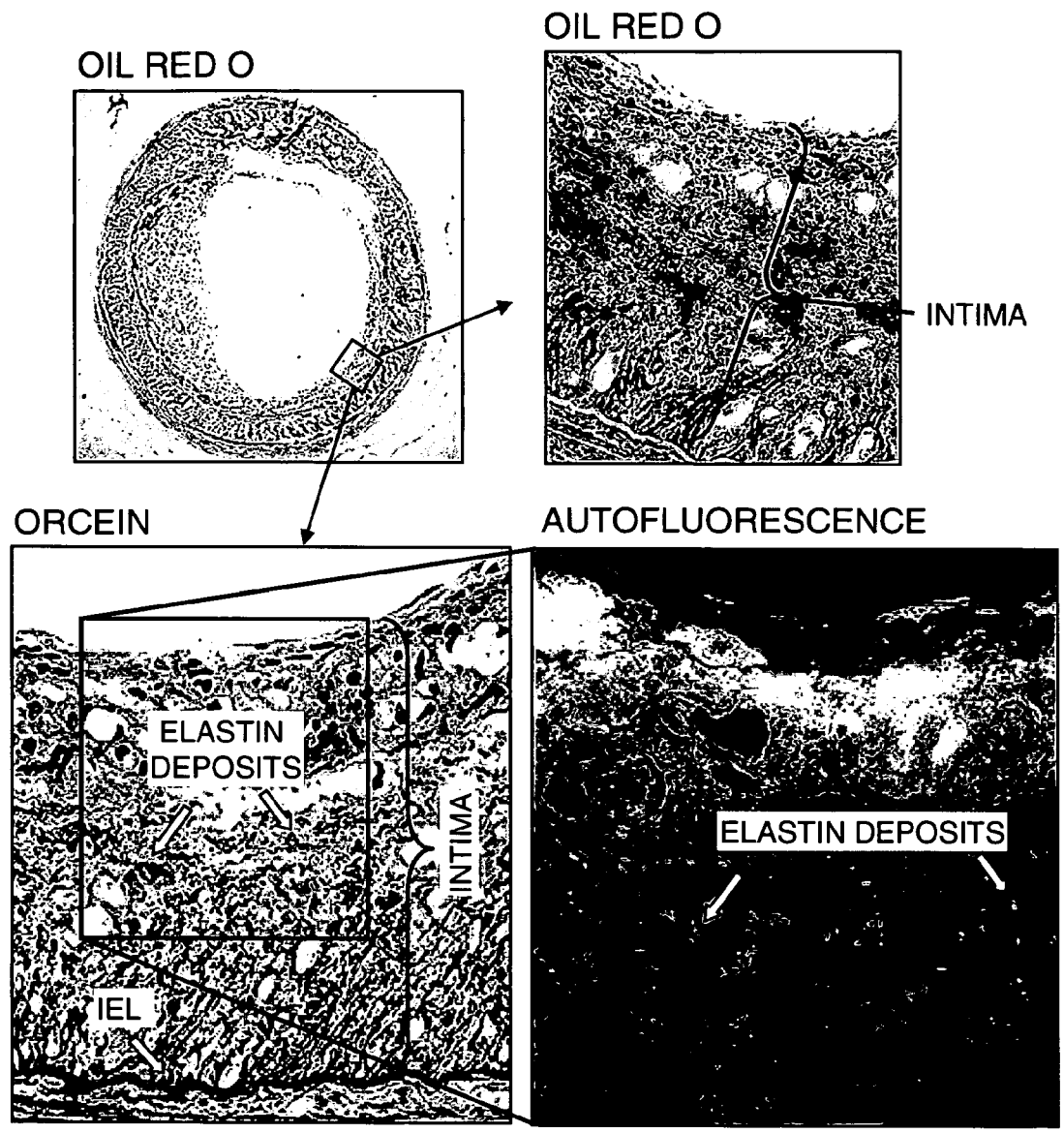
Figures 2, 3, 4, 5, 6, 7, 8:
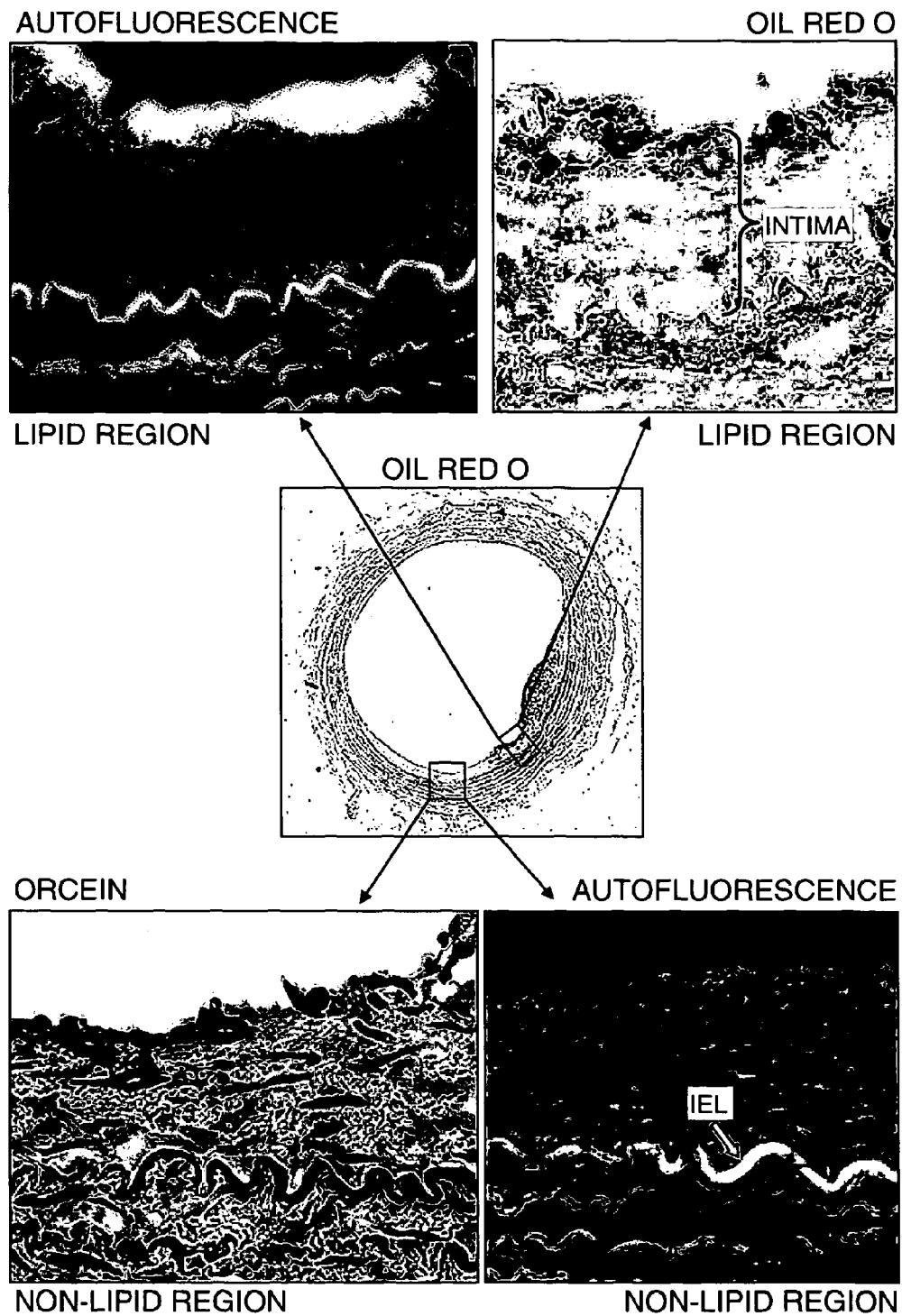
Figures 2, 3, 4, 5, 6, 7, 8, 9:
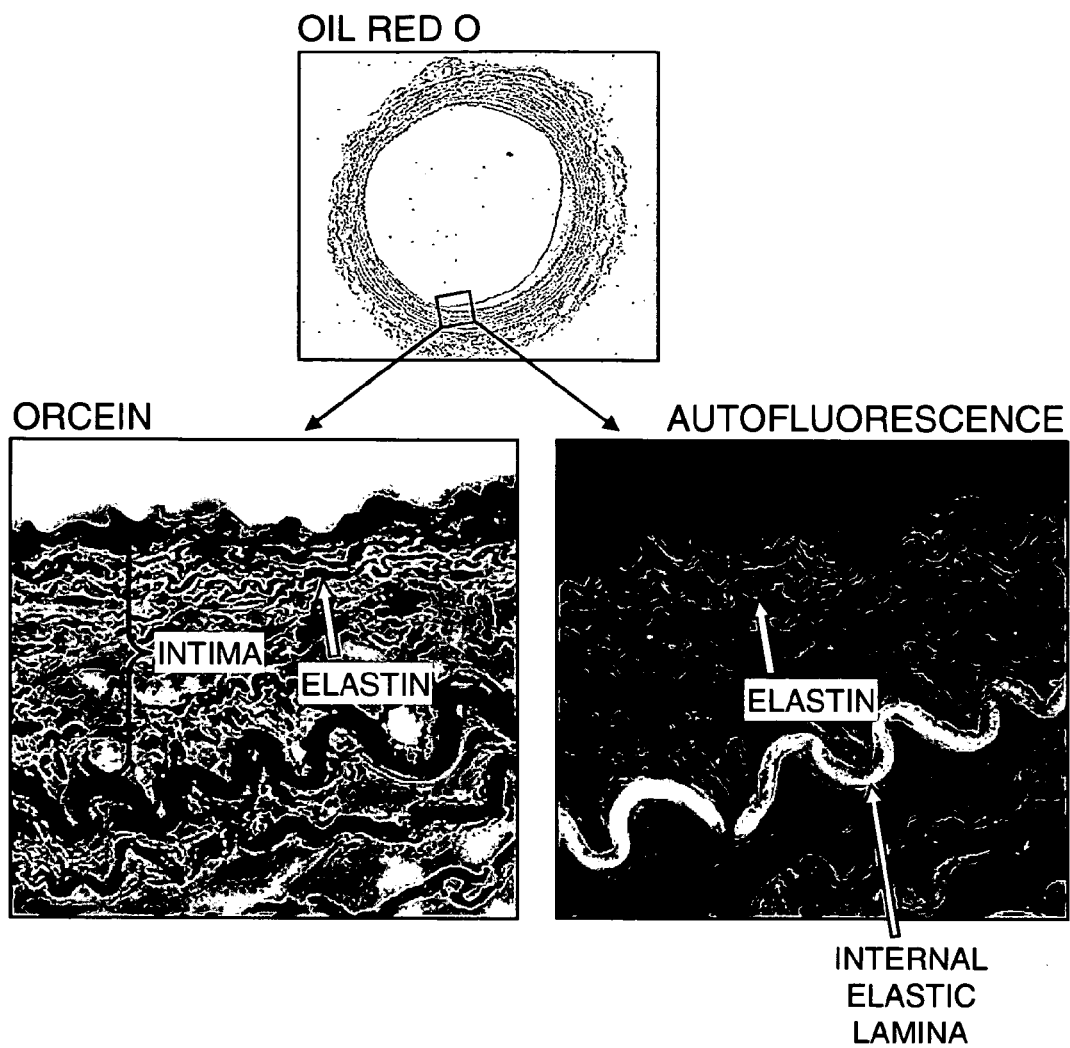
Figure 3A:
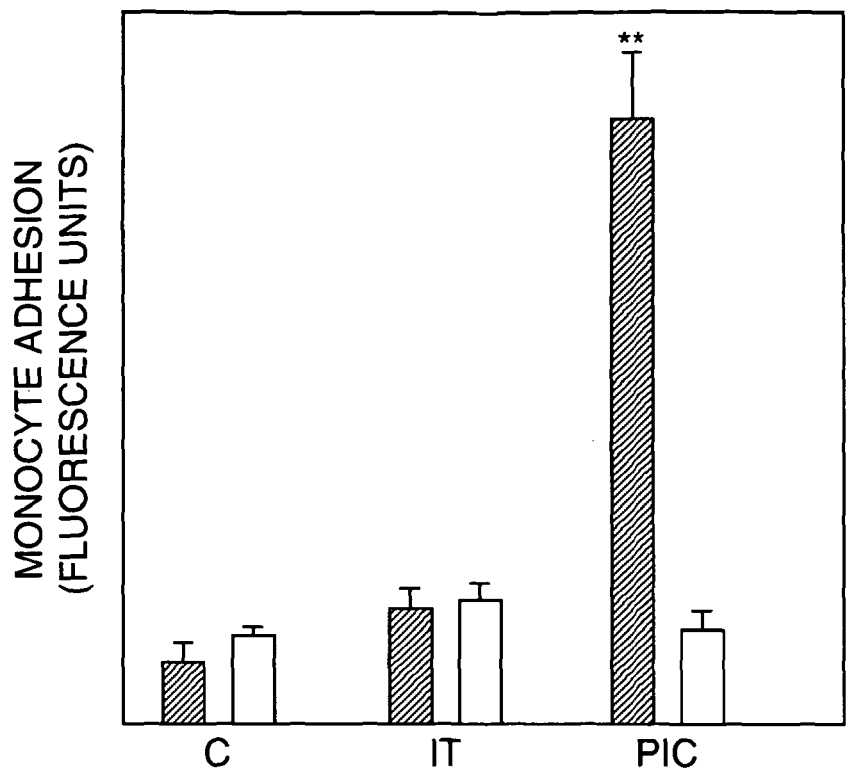
FIG. 3A. Poly I:C increases monocyte adhesion to HLF cultures while IL-1β plus TNFα does not. Fluorescently labeled U937 monocytes were incubated with HLF cultures for 90 min at 4° C. after 24 h exposure of the HLF to 10% FBS-containing medium with poly I:C, IL-1β plus TNFα, or no addition. Some wells were treated with hyaluronidase for 20-30 min prior to addition of monocytes. Open bars=plus hyaluronidase.
Figure 3B:
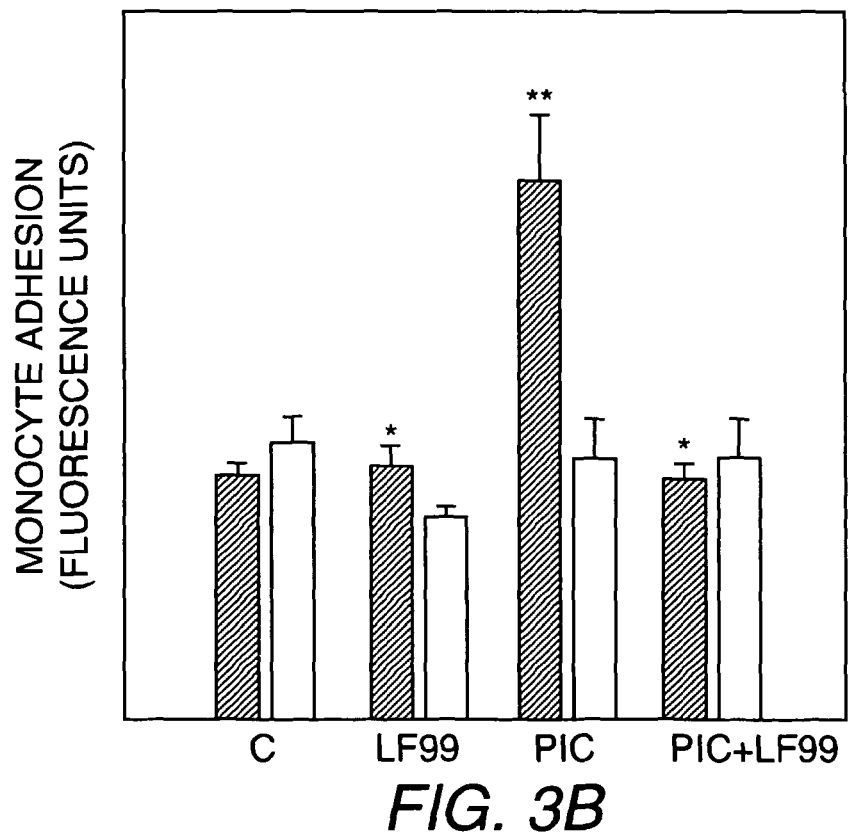
FIG. 3B. Formation of a poly I:C-induced monocyte-retaining ECM can be blocked by the addition of an antibody to versican. HLF were stimulated with poly I:C in 10% FBS-containing medium for 24 h in the presence or absence of an antibody to the N-terminus of versican (Bernstein E F, Fisher L W, Li K, LeBaron R G, Tan E M, Uitto J. Differential expression of the versican and decorin genes in photoaged and sun-protected skin. Comparison by immunohistochemical and northern analyses. *Lab Invest* 1995; 72:662-669). The subsequent monocyte binding assay was carried out in the absence of those blockers. Complete inhibition of hyaluronidase sensitive monocyte binding was observed. C. Inhibition of ECM formation by anti-versican antibody. Open bars=plus hyaluronidase. *P<0.05 compared to poly I:C, **P<0.01 compared to controls. Monocyte binding was measured as arbitrary fluorescence units, reflecting Calcein AM in the cells. Fluorescence was linearly associated with monocyte number (data not shown).
Figure 4:
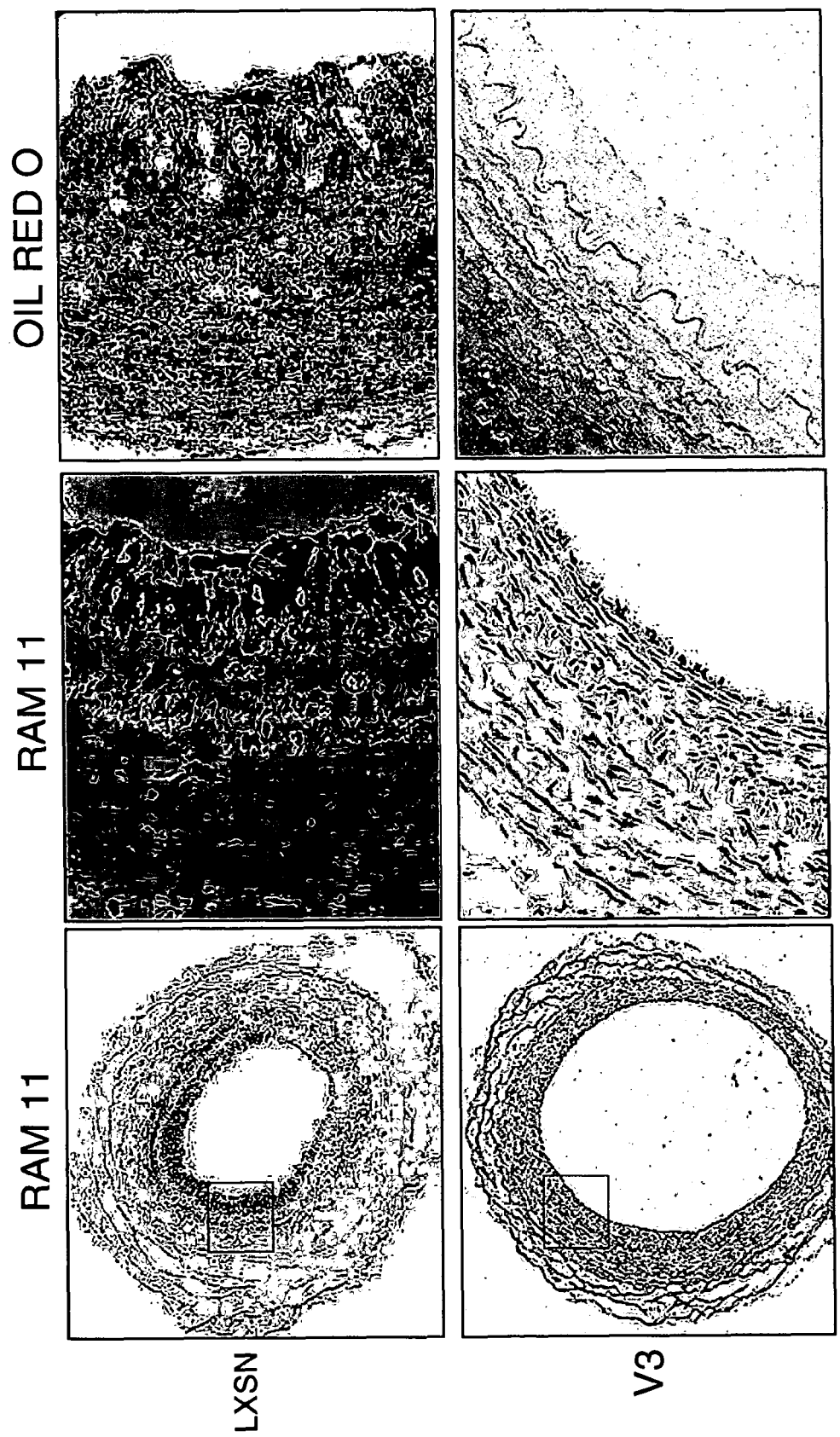

Addition of an antibody to the N-terminal of versican, LF99, during matrix formation, completely blocked the poly I:C-induced and hyaluronidase sensitive binding of monocytes to human lung fibroblasts (HLF) (FIG. 3B).

Example 4

Reduced Macrophage Involvement and Inflammation in V3 Seeded Ballooned Vessels

New Zealand White rabbit vascular smooth muscle cells were retrovirally transduced with versican variant V3 or with the empty vextor (LXSN) and the cells seeded into balloon-injured right carotid arteries of New Zealand White rabbits. Approximately 55×10³ cells were introduced into each common carotid, in an approximately 2 cm section isolated by ligatures, and left for 15 minutes to allow the cells to attach to the endothelial cell-denuded wall. Following restoration of blood flow and recover from the surgery, animals were maintained on a normal chow diet for four weeks followed by a cholesterol enriched diet for a further four weeks (0.15% cholesterol for two weeks, 0.3% for two weeks). Average plasma cholesterol levels for both groups at the end of the 8 week period were ~25 mmol/l. Following termination, vessels were perfusion fixed at systolic blood pressure in 2.5% paraformaldehyde and collected for light and electron microscopy processing. Histological sections were stained for elastin (orcein), lipid (Oil red O), chondroitin sulphate proteoglycans (9BA12 antibody) and macrophages (RAM 11 antibody). Neointimae of the V3 seeded vessels were significantly thinner, and contained less lipid, more elastin, and fewer macrophages than control (LXSN) neointimae. There was a strong correlation between lipid-rich lesions, and macrophage involvement which was most notable in the lesion-rich control carotids (see FIG. 4). V3 neointimae contained fewer lesions and fewer macrophages, and often there was a complete absence of lipid and macrophages (see Figure). When present, however, there was again a strong correlation between lipid deposits and macrophages. These areas, in both controls and V3 animals also contained increased amounts of chondroitin sulphate proteoglycans which have been shown to trap and bind lipid. These findings point to V3 as an anti-inflammatory molecule that also alters the balance of extracellular matrix components to create an elastin-rich lipid-resistant inner vessel wall.

REFERENCES

Miosge N, Sasaki T, Chu M L, Herken R, Timpl R. Ultrastructural localization of microfibrillar fibulin-1 and fibulin-2 during heart development indicates a switch in molecular associations. *Cell Mol Life Sci.* 1998 54(6):606-13.

Faggian J, Fosang A J, Zieba M, Wallace M J, Hooper S B. Changes in versican and chondroitin sulfate proteoglycans during structural development of the lung. *Am J Physiol Regul Integr Comp Physiol.* 2007 293(2):R784-92.

Dunning K R, Lane M, Brown H M, Yeo C, Robker R L, Russell D L. Altered composition of the cumulus-oocyte complex matrix during in vitro maturation of oocytes. *Hum Reprod.* 2007 Sep. 13; [Epub ahead of print]

Irving-Rodgers H F, Rodgers R J. Extracellular matrix of the developing ovarian follicle. *Semin Reprod Med.* 2006 24(4):195-203.

Wight T N. Versican: a versatile extracellular matrix proteoglycan in cell biology. *Curr Opin Cell Biol.* 2002 14(5):617-23.

Wight T N, Lara S, Riessen R, Le Baron R, Isner J. Selective deposits of versican in the extracellular matrix of restenotic lesions from human peripheral arteries. *Am J Pathol.* 1997 151(4):963-73.

Geary R L, Nikkari S T, Wagner W D, Williams J K, Adams M R, Dean R H. Wound healing: a paradigm for lumen narrowing after arterial reconstruction. *J Vasc Surg.* 1998 27(1):96-106

Ricciardelli C, Russell D L, Ween M P, Mayne K, Suwiwat S, Byers S, Marshall V R, Tilley W D, Horsfall D J. Formation of hyaluronan- and versican-rich pericellular matrix by prostate cancer cells promotes cell motility. *J Biol Chem.* 2007 282(14):10814-25.

Ricciardelli C, Mayne K, Sykes P J, Raymond W A, McCaul K, Marshall V R, Horsfall D J. Elevated levels of versican but not decorin predict disease progression in early-stage prostate cancer. *Clin Cancer Res.* 1998 4(4):963-71.

Suwiwat S, Ricciardelli C, Tammi R, Tammi M, Auvinen P, Kosma V M, LeBaron R G, Raymond W A, Tilley W D, Horsfall D J. Expression of extracellular matrix components versican, chondroitin sulfate, tenascin, and hyaluronan, and their association with disease outcome in node-negative breast cancer. *Clin Cancer Res.* 2004 10(7):2491-8.

Pirinen R, Leinonen T, Bohm J, Johansson R, Ropponen K, Kumpulainen E, Kosma V M. Versican in nonsmall cell lung cancer: relation to hyaluronan, clinicopathologic factors, and prognosis. *Hum Pathol.* 2005 36(1):44-50.

Ricciardelli C, Rodgers R J. Extracellular matrix of ovarian tumors. *Semin Reprod Med.* 2006 24(4):270-82.

Wu Y, Chen L, Cao L, Sheng W, Yang B B. Overexpression of the C-terminal PG-M/versican domain impairs growth of tumor cells by intervening in the interaction between epidermal growth factor receptor and beta1-integrin. *J Cell Sci.* 2004 117(Pt 11):2227-37.

Xiang Y Y, Dong H, Wan Y, Li J, Yee A, Yang B B, Lu W Y. Versican G3 domain regulates neurite growth and synaptic transmission of hippocampal neurons by activation of epidermal growth factor receptor. *J Biol Chem.* 2006 281(28): 19358-68.

Turley E A, Noble P W, Bourguignon L Y. Signaling properties of hyaluronan receptors. *J Biol Chem.* 2002 277(7): 4589-92.

Fire A, Xu S, Montgomery M K, Kostas S A, Driver S E, Mello C C. Potent and specific genetic interference by double-stranded RNA in *Caenorhabditis elegans*. *Nature* (1998) 391:806-811.

Horiuchi A, Nikaido T, Mitsushita J, Toki T, Konishi I, Fujii S. Enhancement of antitumor effect of bleomycin by low-voltage in vivo electroporation: a study of human uterine leiomyosarcomas in nude mice. *Int J Cancer* 2000 88(4): 640-4.

Fogh J and Trempe G. *Human Tumor Cells in Vitro.* J. Fogh, editor; Plenum Publishing Corp., New York, 1975, pp. 115-41.

Fletcher C D M: *World Health Organization Classification of Tumours. Pathology and genetics of tumours of soft tissue and bone*. Vol. 5. Edited by Fletcher C D M, Unni K, and Mertens K. Lyon, France: IARC Press; 2002.

Guillou L, Coindre J M, Bonichon F, Nguyen B B, Terrier P, Collin F, Vilain M O, Mandard A M, Le Doussal V, Leroux A, Jacquemier J, Duplay H, Sastre-Garau X, Costa J. Comparative study of the National Cancer Institute and French Federation of Cancer Centers Sarcoma Group grading systems in a population of 410 adult patients with soft tissue sarcoma. *J Clin Oncol* 1997 15(1):350-62.

Hyacinthe M, Jaroszeski M J, Dang V V, Coppola D, Karl R C, Gilbert R A, Heller R. Electrically enhanced drug delivery for the treatment of soft tissue sarcoma. *Cancer* 1999 85(2):409-17.

Cattaruzza S, Perris R. Proteoglycan control of cell movement during wound healing and cancer spreading. *Matrix Biology* 2005 24(6):400-17.

Cattaruzza S, Schiappacassi M, Kimata K, Colombatti A, Perris R. The globular domains of PG-M/versican modulate the proliferation-apoptosis equilibrium and invasive capabilities of tumor cells. *FASEB J* 2004 18(6):779-81.

Cattaruzza S, Schiappacassi M, Ljungberg-Rose A, Spessotto P, Perissinotto D, Morgelin M, Mucignat M T, Colombatti A, Perris R. Distribution of PG-M/versican variants in human tissues and de novo expression of isoform V3 upon endothelial cell activation, migration, and neoangiogenesis in vitro. *J Biol Chem.* 2002 277(49):47626-35.

Kodama J, Hasengaowa, Kusumoto T, Seki N, Matsuo T, Nakamura K, Hongo A, Hiramatsu Y. Versican expression in human cervical cancer. *Eur J Cancer.* 2007 43(9):1460-6.

Skandalis S S, Theocharis A D, Papageorgakopoulou N, Vynios D H, Theocharis D A. The increased accumulation of structurally modified versican and decorin is related with the progression of laryngeal cancer. *Biochimie* 2006 88(9):1135-43.

Skandalis S S, Theocharis A D, Theocharis D A, Papadas T, Vynios D H, Papageorgakopoulou N. Matrix proteoglycans are markedly affected in advanced laryngeal squamous cell carcinoma. *Biochim Biophys Acta.* 2004 1689 (2):152-61.

Labropoulou V T, Theocharis A D, Ravazoula P, Perimenis P, Hjerpe A, Karamanos N K, Kalofonos H P. Versican but not decorin accumulation is related to metastatic potential and neovascularization in testicular germ cell tumours. *Histopathology.* 2006 49(6):582-93.

Tsara M E, Theocharis A D, Theocharis D A. Compositional and structural alterations of proteoglycans in human rectum carcinoma with special reference to versican and decorin. *Anticancer Res.* 2002 22(5): 2893-8.

Aruffo A, Stamenkovic I, Melnick M, Underhill C B, Seed B. CD44 is the principal cell surface receptor for hyaluronate. *Cell* 1990 61:1303-13

Goldstein L A, Zhou D F, Picker L J, Minty C N, Bargatze R F, Ding J F, and Butcher E C. A human lymphocyte homing receptor, the hermes antigen, is related to cartilage proteoglycan core and link proteins. *Cell* 1989 56:1063-1072.

Bourguignon L Y, Gilad E, Peyrollier K. Heregulin-mediated ErbB2-ERK signaling activates hyaluronan synthases leading to CD44-dependent ovarian tumor cell growth and migration. *J Biol Chem.* 2007 282(27):19426-41.

Sheng W, Wang G, Wang Y, Liang J, Wen J, Zheng P S, Wu Y, Lee V, Slingerland J, Dumont D, Yang B B. The roles of versican V1 and V2 isoforms in cell proliferation and apoptosis. *Mol Biol Cell.* 2005 16(3):1330-40.

Wu Y, Chen L, Cao L, Sheng W, Yang B B. Overexpression of the C-terminal PG-M/versican domain impairs growth of tumor cells by intervening in the interaction between epidermal growth factor receptor and beta1-integrin. *J Cell Sci.* 2004 117(Pt 11):2227-37.

Wu Y, Zhang Y, Cao L, Chen L, Lee V, Zheng P S, Kiani C, Adams M E, Ang L C, Paiwand F, Yang B B. Identification of the motif in versican G3 domain that plays a dominant-negative effect on astrocytoma cell proliferation through inhibiting versican secretion and binding. *J Biol Chem.* 2001 276(17):14178-86.

Zheng P S, Wen J, Ang L C, Sheng W, Viloria-Petit A, Wang Y, Wu Y, Kerbel R S, Yang B B. Versican/PG-M G3 domain promotes tumor growth and angiogenesis. *FASEB J.* 2004 18(6):754-6.

Nikitovic D, Zafiropoulos A, Katonis P, Tsatsakis A, Theocharis A D, Karamanos N K, Tzanakakis G N. Transforming growth factor-beta as a key molecule triggering the expression of versican isoforms v0 and v1, hyaluronan synthase-2 and synthesis of hyaluronan in malignant osteosarcoma cells. *IUBMB Life.* 2006 58(1):47-53.

Underhill C B, Nguyen H A, Shizari M, Culty M. CD44 positive macrophages take up hyaluronan during lung development. *Dev. Biol.* 1993 155:324-336.

Chomczynski, P. A reagent for the single-step simultaneous isolation of RNA, DNA and proteins from cell and tissue samples. *Biotechniques* 1993 15:532-4, 536-7.

Lemire J M, Merrilees M J, Braun K R, Wight T N. Overexpression of the V3 variant of versican alters arterial smooth muscle cell adhesion, migration, and proliferation in vitro. *J Cell Physiol.* 2002 190: 38-45.

Robboy S J, Kumudini M, Norris H J. Malignant potential and pathology of leiomyomatous tumors of the uterus. *Clin. Consult. Obstet. Gynecol.* 1990 1:2-9.

Perrone T and Delmer L P. Prognostically favorable "mitotically active" smooth-muscle tumors of the uterus. *Am. J. Surg. Pathol.* 1988 12(1):1-8.

Jones M W and Norris H J. Clinicopathologic study of 28 uterine leiomyosarcomas with metastasis. *Int. J Gynecol. Pathol.* 1995 14:243-249.

The foregoing is illustrative of the present invention, and is not to be construed as limiting thereof. The invention is defined by the following claims, with equivalents of the claims to be included therein.

That which is claimed is:

1. A method of treating restenosis in a subject in need thereof, comprising administering said subject a versican inhibitor in an amount effective to inhibit arterial restenosis, wherein said versican inhibitor is an siRNA molecule that inhibits expression of versican isoform V0 and/or versican isoform V1 in said subject;
wherein said siRNA molecule is directed to the versican G1 region.

2. The method of claim 1, wherein said siRNA molecule comprises a double-stranded segment 15-60 nucleotides in length.

3. The method of claim 1, wherein said siRNA molecule inhibits expression of versican isoform V0.

4. The method of claim 1, wherein said siRNA molecule inhibits expression of versican isoform V1.

5. The method of claim 2, wherein said siRNA molecule inhibits expression of versican isoform V0 and versican isoform V1.

* * * * *

UNITED STATES PATENT AND TRADEMARK OFFICE
CERTIFICATE OF CORRECTION

PATENT NO.       : 8,410,067 B2  
APPLICATION NO.  : 12/677435  
DATED            : April 2, 2013  
INVENTOR(S)      : Wight et al.

Page 1 of 1

It is certified that error appears in the above-identified patent and that said Letters Patent is hereby corrected as shown below:

In the Claims:
Column 32, Claim 5, Line 23: correct "The method of claim 2, wherein"
to read -- The method of claim 1, wherein --

Signed and Sealed this
Twenty-second Day of April, 2014

Michelle K. Lee
*Deputy Director of the United States Patent and Trademark Office*